US012589155B2

(12) United States Patent
Low et al.

(10) Patent No.: US 12,589,155 B2
(45) Date of Patent: Mar. 31, 2026

(54) EFFICIENT SYNTHESIS OF LIPID-FLUORESCEIN CONJUGATES FOR CAR-T CELL THERAPY

(71) Applicant: Purdue Research Foundation, West Lafayette, IN (US)

(72) Inventors: Philip Stewart Low, West Lafayette, IN (US); Madduri Srinivasarao, West Lafayette, IN (US)

(73) Assignee: Purdue Research Foundation

( * ) Notice: Subject to any disclaimer, the term of this patent is extended or adjusted under 35 U.S.C. 154(b) by 1017 days.

(21) Appl. No.: 17/625,066

(22) PCT Filed: Jul. 2, 2020

(86) PCT No.: PCT/US2020/040723
§ 371 (c)(1),
(2) Date: Jan. 5, 2022

(87) PCT Pub. No.: WO2021/007109
PCT Pub. Date: Jan. 14, 2021

(65) Prior Publication Data
US 2022/0280648 A1 Sep. 8, 2022

Related U.S. Application Data

(60) Provisional application No. 62/870,926, filed on Jul. 5, 2019.

(51) Int. Cl.
*A61K 47/54* (2017.01)
*A61K 41/00* (2020.01)

(52) U.S. Cl.
CPC ........ *A61K 47/544* (2017.08); *A61K 41/0042* (2013.01); *A61K 47/545* (2017.08)

(58) Field of Classification Search
USPC ........................................................... 514/77
See application file for complete search history.

(56) References Cited

U.S. PATENT DOCUMENTS

2011/0251404 A1 10/2011 Nagano et al.
2013/0137720 A1 5/2013 Wang et al.
2018/0100026 A1* 4/2018 Kim .................. A61K 40/4212
2018/0162948 A1* 6/2018 Morrison ............ A61K 38/215

FOREIGN PATENT DOCUMENTS

CN 114340643 4/2022
IN 202217002383 3/2022
JP 2022538909 9/2022
WO WO-2005103282 A1 11/2005
WO 2018148224 8/2018
(Continued)

OTHER PUBLICATIONS

Jóźwiak Effect of medium chain fatty acid in human health and disease Eur. J. Pharmacol., 2020 871 172937 (Year: 2020).*
(Continued)

*Primary Examiner* — Michael G. Hartley
(74) *Attorney, Agent, or Firm* — Schwegman Lundberg & Woessner, P.A.

(57) ABSTRACT

Lipid-fluorescein conjugates, the compositions comprising same, and the methods of synthesis and use, such as in the treatment of cancer, are disclosed.

16 Claims, 12 Drawing Sheets

FITC THAT BINDS WITH ANTI-FITC scFv

LIPID TO TARGET CANCER CELLS

FL-PLE

(56) References Cited

FOREIGN PATENT DOCUMENTS

| | | | | |
|---|---|---|---|---|
| WO | WO-2018148224 A1 * | 8/2018 | ......... | A61K 39/0011 |
| WO | WO-2021007109 A1 | 1/2021 | | |

OTHER PUBLICATIONS

Pastuch-Gawołek, A Small Sugar Molecule with Huge Potential in Targeted Cancer Therapy Pharmaceutics 2023, 15, 913 (Year: 2023).*
Zhang, FASEB J. 1991, 5, 3108-3113 (Year: 1991).*
Demchenko et al Photobleaching of organic fluorophores: quantitative characterization, mechanisms, protection Methods Appl. Fluoresc 2020 8 022001 1-25 (Year: 2020).*
Irby Lipid Drug Conjugate for Enhancing Drug Delivery Molecular Pharmaceutics 2017 14 1325-1338 (Year: 2017).*
Jozwiak Anticancer activities of fatty acids and their heterocyclic derivatives Eur. J. Pharma col. 2020 87 104724 (Year: 2020).*
Klan Photoremovable Protecting Groups in Chemistry and Biology: Reaction Mechanisms and Efficacy Chemical Reviews 2012 113 1 119-191 (Year: 2012).*
Pastuch-Gawotek "A Small Sugar Molecule with Huge Potential in Targeted Cancer Therapy", Pharmaceutics 2023, 15, 913 (Year: 2023).*
"International Application Serial No. PCT US2020 040723, International Preliminary Report on Patentability mailed Jan. 20, 2022", 8 pgs.
"Israel Application Serial No. 289597, Notification Prior to Examination mailed Aug. 9, 2022", w o English Translation, 2 pgs.
"European Application Serial No. 20836189.9, Response to Communication Pursuant to Rules 161 and 162 EPC filed Aug. 4, 2022", 14 pgs.
"Chinese Application Serial No. 202080049454.1, Response filed Sep. 22, 2023 to Office Action mailed Aug. 19, 2023", w English claims, 7 pgs.
"European Application Serial No. 20836189.9, Response filed Dec. 13, 2023 to Extended European Search Report mailed May 26, 2023", 19 pgs.
"Chinese Application Serial No. 202080049454.1, Office Action mailed Jan. 27, 2024", W English Translation, 24 pgs.
"Japanese Application Serial No. 2022-500020, Notification of Reasons for Refusal mailed Apr. 25, 2024", w English translation, 10 pgs.
"Canadian Application Serial No. 3,145,290, Voluntary Amendment Filed Jul. 2, 2024", 12 pgs.
"Chinese Application Serial No. 202080049454.1, Response filed Jul. 29, 2024 to Office Action mailed Jan. 27, 2024", W English Claims, 17 pgs.
"Singapore Application Serial No. 11202114062U, Written Opinion mailed Jul. 3, 2024", 9 pgs.
"Chinese Application Serial No. 202080049454.1, Office Action mailed Aug. 20, 2024", w English translation, 24 pgs.
"Israel Application Serial No. 289597, Office Action mailed Sep. 22, 2024", w English Translation, 5 pgs.
Dan, Krishna, "DNA nanodevices map enzymatic activity in organelles", Nature Nanotechnology, vol. 14, No. 3, (Mar. 2019), 21 pgs.
Fang, R. H., "Lipid-insertion enables targeting functionalization of erythrocyte membrane-cloaked nanoparticles", Nanoscale, 2013, 5, 8884, (2013), 5 pgs.
"International Application Serial No. PCT/US2020/040723, International Search Report mailed Nov. 20, 2020", 4 pgs.
"International Application Serial No. PCT/US2020/040723, Invitation to Pay Additional Fees and Partial Search Report mailed Sep. 23, 2020", 3 pgs.
"International Application Serial No. PCT/US2020/040723, Written Opinion mailed Nov. 20, 2020", 6 pgs.
"PubChem-CID-121293291 for the Structure of C12FDG", 26 pgs.
"PubChem-CID-18730 for the Struction of FITC", 9 pgs.
Fang, et al., "Lipid-insertion enables targeting functionalization of erythrocyte membrane-cloaked nanoparticles", 5 pgs.
"Japanese Application Serial No. 2022-500020, Voluntary Amendment filed May 18, 2023", w English claims, 16 pgs.
"European Application Serial No. 20836189.9, Extended European Search Report mailed May 26, 2023", 14 pgs.
"Korean Application Serial No. 10-2022-7003639, Voluntary Amendment filed Jun. 30, 2023", w English claims, 29 pgs.
"Brazilian Application Serial No. BR112022000120-7, Voluntary Amendment filed Jun. 30, 2023", w English claims, 61 pgs.
"Indian Application Serial No. 202217002383, Voluntary Amendment filed Jul. 21, 2023", 20 pgs.
"Chinese Application Serial No. 202080049454.1, Office Action mailed Aug. 19, 2023", w English Translation, 2 pages.
Banks, Peter R, "Comparison of Three Common Amine Reactive Fluorescent Probes Used for Conjugation to Biomolecules by Capillary Zone Electrophoresis", Bioconjugate Chemistry, vol. 6, No. 4, (Jul. 1, 1995), 12 pgs.
Christopher, J Cheng, "Enhanced siRNA delivery into cells by exploiting the synergy between targeting ligands and cell-penetrating peptides", Biomaterials, Elsevier, Amsterdam, NL, vol. 32, No. 26, (Apr. 20, 2011), 10 pgs.
Dan, Krishna, "Dna nanodevices map enzymatic activity in organelles", Nature Nanotechnology, Nature Pub. Group, Inc, London, vol. 14, No. 3, (Feb. 11, 2019), 13 pgs.
Dan, Krishna, "DNA nanodevices map enzymatic activity in organelles—supplementary information", Nature Nanotechnology, vol. 14, No. 3,, [Online] Retrieved from the internet:http : www.nature.com articles $41565-019-0365-6, (Feb. 11, 2019), 26 pgs.
"Chinese Application Serial No. 202080049454.1, Response Filed Oct. 21, 2024 to Office Action mailed Aug. 20, 2024", w English claims, 17 pgs.
"Japanese Application Serial No. 2022-500020, Response filed Oct. 23, 2024 to Notification of Reasons for Refusal mailed Apr. 25, 2024", w English translation, 28 pgs.
"Chinese Application Serial No. 202080049454.1, Decision of Rejection mailed Nov. 2, 2024", W English Translation, 17 pgs.
"Japanese Application Serial No. 2022-500020, Notification of Reasons for Rejection mailed Jan. 20, 2025", w English Translation, 6 pgs.
"Singapore Application Serial No. 11202114062U, Response filed Dec. 3, 2024 to Written Opinion mailed Jul. 3, 2024", 16 pgs.
"Israel Application Serial No. 289597, Response filed Jan. 22, 2025 to Office Action mailed Sep. 22, 2024", w English claims, 12 pgs.
"Chinese Application Serial No. 202080049454.1, Response filed Feb. 5, 2025 to Decision of Rejection mailed Nov. 2, 2024", w English claims, 33 pgs.
"Japanese Application Serial No. 2022-500020, Response filed Mar. 27, 2025 to Notification of Reasons for Rejection mailed Jan. 20, 2025", w English translation and current English claims, 18 pgs.
"Japanese Application Serial No. 2022-500020, Notification of Reasons for Refusal mailed May 12, 2025", w English Translation, 6 pgs.
"New Zealand Application Serial No. 783776, Voluntary Amendment filed Jul. 2, 2025", 44 pgs.
"Chinese Application Serial No. 202080049454.1, Notice of Reexamination mailed Jul. 13, 2025", W English Translation, 18 pgs.
"Japanese Application Serial No. 2022-500020, Response filed Jul. 28, 2025 to Notification of Reasons for Refusal mailed May 12, 2025", w English claims, 14 pgs.

* cited by examiner

FL-PLE

PRO-FL-PLE

PURDUE FL-PLE (MS-109)

PURDUE PRO-FL-PLE (MS-115)

FB35462, Carbosynth
4-(Bromomethyl)benzylamine HBr

D-5100 - N,N-Dimethylcephalin octadecyl ester
Biosynth.com

MS-100

FITC, F7250 Sigma-Aldrich

MS-115

MS-109

D

Ref: Journal of Biological Chemistry 2003 278(5) 3170-3175; PCT 2018148224

E

Ref: Chromatographia 2016 v.79 no.5-6 pp. 319-325

Doubly activated (logic gate)

EFFICIENT SYNTHESIS OF LIPID-FLUORESCEIN CONJUGATES FOR CAR-T CELL THERAPY

CROSS REFERENCE TO RELATED APPLICATION

This application is a U.S. national stage filing under 35 U.S.C. 371 from International Application No. PCT/US2020/040723, filed on 2 Jul. 2020, and published as WO 2021/007109 on 14 Jan. 2021, which claims priority to U.S. provisional patent application No. 62/870,926, which was filed on Jul. 5, 2019, which are hereby incorporated by reference in their entireties.

TECHNICAL FIELD

This disclosure relates to lipid-fluorescein conjugates, compositions comprising same, and methods of synthesis and use, such as in the treatment of cancer, e.g., CAR-T cell therapy.

BACKGROUND

Glioma is one of the most common cancers in children. Because of its heterogeneity, glioma doesn't present a single prominent antigen. Therefore, a chimeric antigen receptor (CAR) T cell therapy against pediatric glioma would require the identification and targeting of a pan-cancer antigen. Recently, a universal anti-FITC (fluorescein isothiocyanate) CAR-T cell was reported, wherein administration of a bispecific adapter molecule that has fluorescein linked to a tumor-specific ligand promotes bridging of the CAR-T cell with a tumor cell, and subsequent CAR-T-cell activation kills the cancer cell. Certain synthetic phospholipid ethers (PLEs) that target specifically cancer cell membrane have been reported. Because they target the cancer cell membrane, itself, they have the potential to become a pan-cancer targeting ligand. These PLEs are known to be rapidly catabolized by normal cells but to persist on tumor cell membranes for a long duration. Further, these PLEs require lengthy synthesis (12-17 steps).

Bispecific adaptor molecules containing PLEs conjugated to fluorescein isothiocyanate (called FL-PLE) were used in combination with anti-FITC CAR-T cells to achieve therapy against glioma (FIG. 1). Polyethylene glycol (PEG3) linker was used to connect the FITC and lipid components. FL-PLE was produced in a 12-step synthesis. To increase the specificity for cancer, an extra level of specificity was introduced in the form of a protecting group on the —OH on the aromatic ring of fluorescein that is selectively cleaved by reactive oxygen species found in cancer, called Pro-FL-PLE (FIG. 2). The Pro-FL-PLE-based imaging agent shows a tumor-to-background ratio of about 1.5 in glioma, suggesting that this protected version can show specificity to cancer tissue when targeted with CAR-T cell therapeutics. The synthesis of Pro-FL-PLE was accomplished in 17 steps.

There remains a need to develop PLE specific to cancer cell membrane with more efficient synthesis. It is an object of the present disclosure to provide such a therapeutic agent. This and other objects and advantages will be apparent from the description provided herein.

SUMMARY

Provided is a compound of Formula (I) or (II):

(I)

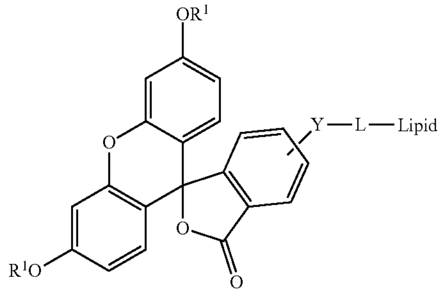

(II)

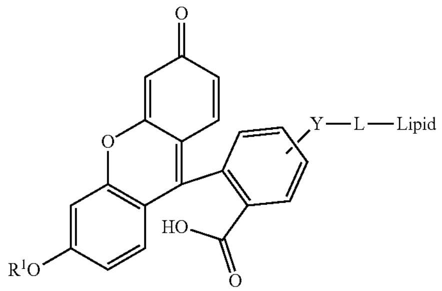

wherein:

$R^1$ is independently H, or a protecting group that is deprotected in tumor extracellular matrix;

Y is absent, —N(H)C(S)N(H)—, —N(H)C(O)N(H)—, —N(H)C(S)—, —C(O)—N(H)—, —C(S)N(H)—, —C(O)O—, —N(H)—, —S(O)N(H)—, $—S(O)_2N(H)—$, $—S(O)_3—$, $—P(O)_2N(H)—$, or $—P(O)_3—$;

L is a linker; and

Lipid is a cancer-cell targeting lipid; and at least one $R^1$ is a protecting group;

or a pharmaceutically acceptable salt thereof.

Further provided is a pharmaceutical composition comprising a compound of Formula (I) or (II) and a pharmaceutically acceptable carrier.

Still further provided is a method of treating cancer comprising administering a compound of Formula (I) or (II) to a subject suffering from cancer.

The disclosure also relates to a method of making a lipid-FITC comprising: reacting a lipid with fluorescein isothiocyanate and a base in a solvent.

The disclosure also relates to a method of making a masked lipid-FITC comprising: reacting a lipid-FITC with a protecting group and a base in a solvent.

DETAILED DESCRIPTION

Figure 1:
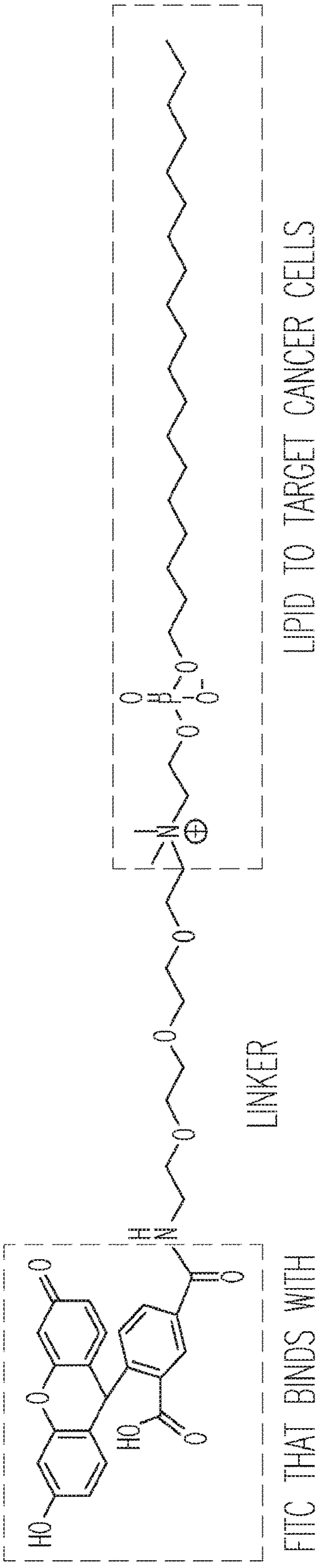
FIG. 1 is the structure of fluorescein-lipid conjugate (FL-PLE).
Figure 2:
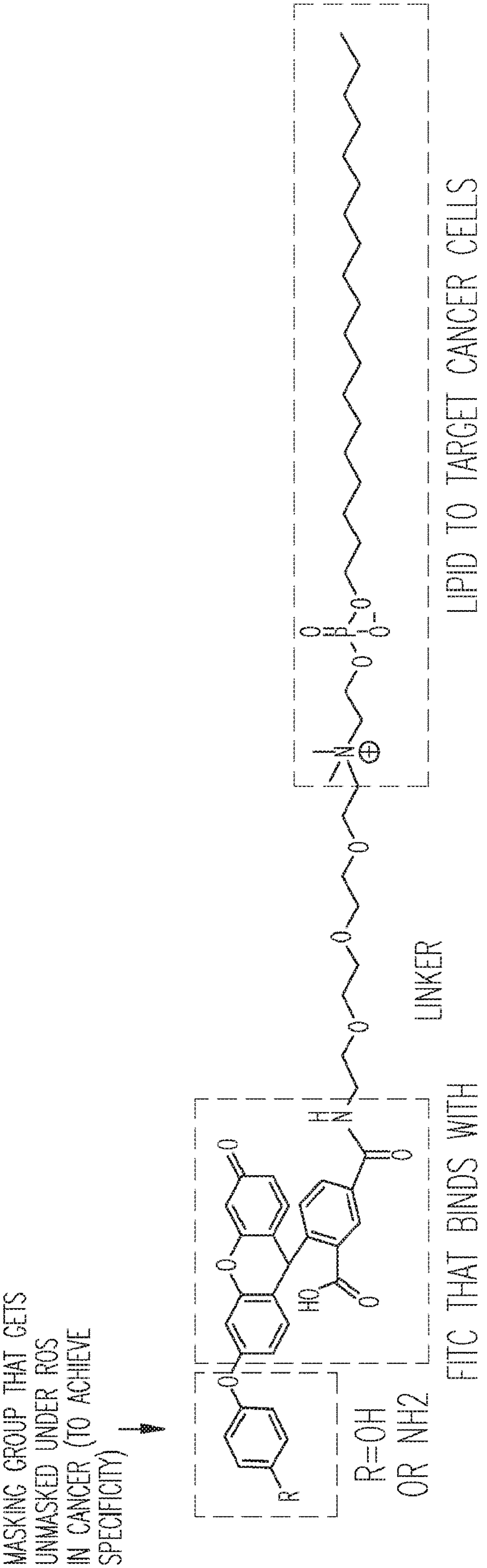
FIG. 2 is the structure of Pro-fluorescein-lipid conjugate (Pro-FL-PLE).

The disclosure provides lipid-fluorescein conjugates, compositions comprising same, and methods of synthesis and use, such as in the treatment of cancer, e.g., CAR-T cell therapy.

Definitions

For convenience, before further description of the present disclosure, some terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present disclosure to be more readily understood, some terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer to A only (optionally including elements other than B); or to B only (optionally including elements other than A); or yet, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, to at least one, optionally including more than one, A, with no B present (and optionally including elements other than B); or to at least one, optionally including more than one, B, with no A present (and optionally including elements other than A); or yet, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to.

Various compounds contained in compositions of the present disclosure may exist in particular geometric or stereoisomeric forms. In addition, polymers of the present disclosure may also be optically active. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this disclosure.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In various embodiments, pharmaceutical compositions of the present disclosure are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present disclosure may contain one or more acidic functional groups and, thus, can form pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the patient of one or more compound of the disclosure. If it is administered prior to clinical manifestation of the unwanted condition (e.g., disease or other unwanted state of the host animal), then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The term "patient" or "subject" refers to a mammal suffering of a disease, disorder, or condition. In various embodiments, a patient or subject is a primate, canine, feline, or equine. In various embodiments, a patient or subject is a bird. In various embodiments, the bird is a domesticated bird, such as chicken. In various embodiments, the bird is a fowl. In various embodiments, a patient or subject is a human. A child patient or subject refers to a human of 18 years of age or less.

For purposes of this disclosure, the chemical elements are identified in accordance with the Periodic Table of the Elements, CAS version, Handbook of Chemistry and Physics, 67th Ed., 1986-87, inside cover.

Compounds

The disclosure relates to a compound of Formula (I) or (II):

(I)

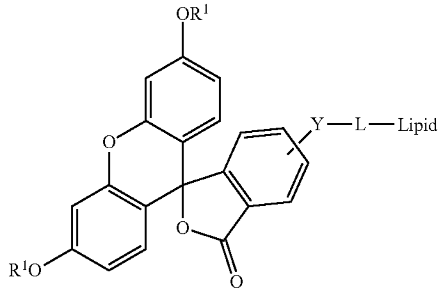

-continued (II)

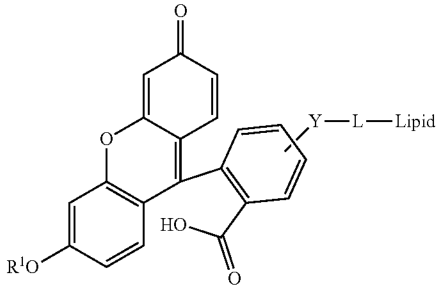

wherein:

- $R^1$ is independently H, or a protecting group that is deprotected in tumor extracellular matrix;
- Y is absent, —N(H)C(S)N(H)—, —N(H)C(O)N(H)—, —N(H)C(O)—, —N(H)C(S)—, —C(O)—N(H)—, —C(S)N(H)—, —C(O)O—, —N(H)—, —S(O)N(H)—, —$S(O)_2N(H)$—, —$S(O)_3$—, —$P(O)_2N(H)$—, or —$P(O)_3$—;
- L is a linker; and
- Lipid is a cancer-cell targeting lipid; and
- at least one $R^1$ is a protecting group;
- or a pharmaceutically acceptable salt thereof.

$R^1$ can be H. $R^1$ can be a protecting group that is deprotected in tumor extracellular matrix. Both $R^1$ can independently be a protecting group. Each $R^1$ can be different. Both $R^1$ can be the same.

The protecting group can be a reactive oxygen species (ROS)-cleavable group. The protecting group can be an acid-cleavable group. The protecting group can be reductively cleaved. The protecting group can be an enzyme-cleavable group. The protecting group can be cleavable at low pH. The protecting group can be cleaved by any triggers in the tumor microenvironment. The protecting group can be

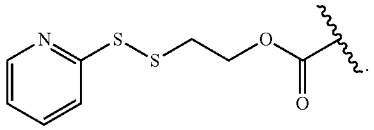 [SMILES: *C(=O)OCCSSc1ccccn1]

The protecting group can be

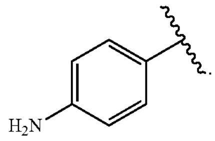

The protecting group can be

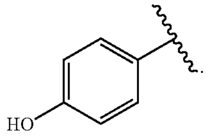 [SMILES: *c1ccc(O)cc1]

Y can be absent. Y can be —N(H)C(S)N(H)—. Y can be —N(H)C(O)N(H)—. Y can be —N(H)C(O)—. Y can be —N(H)C(S)—. Y can be —C(O)—N(H)—. Y can be —C(S)N(H)—. Y can be —C(O)O—. Y can be —N(H)—. Y can be —S(O)N(H)—. Y can be —$S(O)_2N(H)$—. Y can be —$S(O)_3$—. Y can be —$P(O)_2N(H)$—. Y can be —$P(O)_3$—.

L can be a UV-active linker. L can be a chromophore. L can be

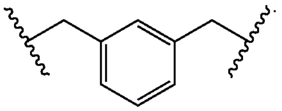 [SMILES: *Cc1cccc(C*)c1]

Lipid can be a lipid comprising 5-30 carbon atoms. Lipid can be

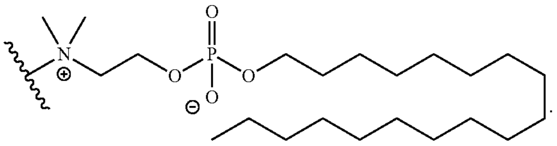 [SMILES: *[N+](C)(C)CCOP(=O)([O-])OCCCCCCCCCCCCCCCCCC]

The compound of Formula (I) can be

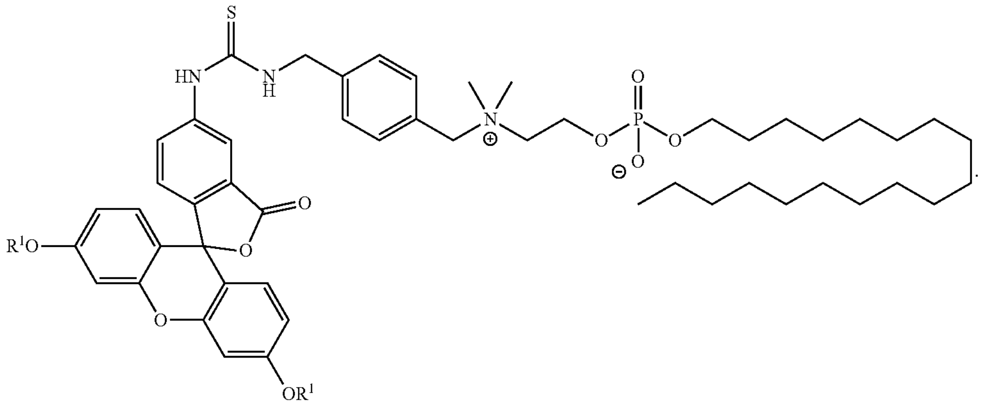

The compound of Formula (I) can be

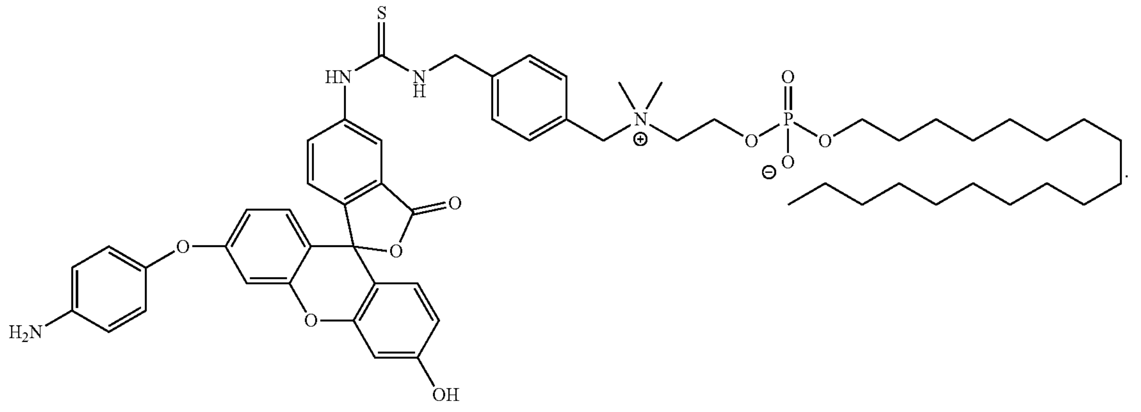 [SMILES: CCCCCCCCCCCCCCCCCCOP(=O)([O-])OCC[N+](C)(C)Cc1ccc(CNC(=S)Nc2ccc3c(c2)C(=O)OC32c3ccc(O)cc3Oc3cc(Oc4ccc(N)cc4)ccc32)cc1]

The compound of Formula (I) can be

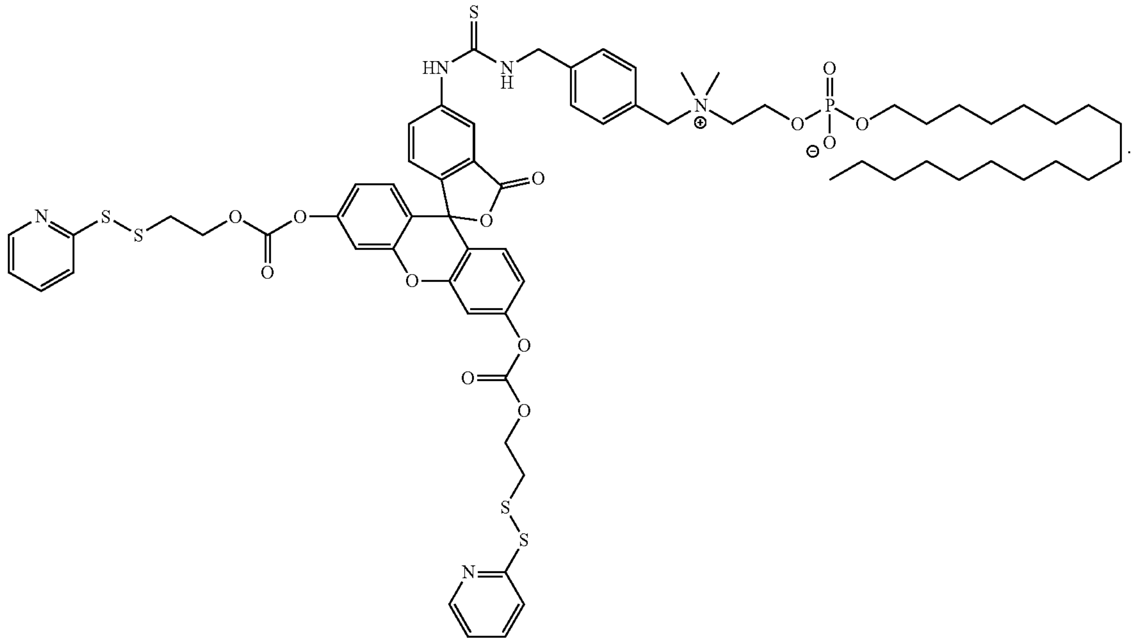 [SMILES: CCCCCCCCCCCCCCCCCCOP(=O)([O-])OCC[N+](C)(C)Cc1ccc(CNC(=S)Nc2ccc3c(c2)C(=O)OC32c3ccc(OC(=O)OCCSSc4ccccn4)cc3Oc3cc(OC(=O)OCCSSc4ccccn4)ccc32)cc1]

Methods of Making Lipid-Fluorescein Conjugates

The disclosure relates to a method of making a lipid-FITC (fluorescein isothiocyanate) comprising:

reacting a lipid with FITC and a base in a solvent.

The disclosure also relates to a method of making a masked lipid-FITC comprising:

reacting a lipid-FITC with a protecting group and a base in a solvent.

The disclosure also relates to a method of making a FITC-PLE with heterogeneous protecting groups comprising:

i) conjugating a lipid to aminobenzyl bromide to produce the quaternary ammonium intermediate, ii) coupling of the intermediate to fluorescein isothiocyanate to produce a xylene-based FL-PLE and iii) optionally protecting a Pro-FL-PLE.

The xylene-based FL-PLE can be MS-109. The Pro-FL-PLE can be MS-115.

The base can be potassium carbonate, sodium carbonate, trialkylamine, pyridine, dimethylaminopyridine, potassium hydroxide, or sodium hydroxide. The base can be DIEA. The base can be potassium carbonate. The base can be pyridine The solvent can be chloroform, tetrahydrofuran, carbon tetrachloride, dichloromethane, dimethyl sulfoxide, dimethyl formamide, acetonitrile, pyridine, water, or any combination of thereof. The solvent can be chloroform-DMSO (2:1). The solvent can be chloroform. The solvent and base can be pyridine.

The compounds of the disclosure, such as compounds Formula (I) or (II), a lipid-FITC, a masked lipid-FITC, or a FITC-PLE with heterogeneous protecting groups can also be synthesized in any way known to one of ordinary skill in the art.

Methods of Treatment

The disclosure relates to a method of treating cancer in a subject suffering therefrom. The method can comprise administering to the subject a therapeutically effective amount of an above-described compound or a pharmaceutical composition comprising same and a pharmaceutically acceptable carrier. The cancer can be glioma.

The compound can be any compound of the disclosure.

A detailed description of how to utilize herein synthesized improved Purdue-FL-PLE in the context of CAR-T cell therapy in cancer is contemplated as described in WO2018148224, the content of which is expressly incorporated herein for reference.

Pharmaceutical Compositions, Routes of Administration, and Dosing

Pharmaceutical compositions are also provided. In an embodiment, the pharmaceutical composition comprises a compound as described herein and a pharmaceutically acceptable carrier. In another embodiment, the pharmaceutical composition comprises a plurality of compounds as described herein and a pharmaceutically acceptable carrier. In yet another embodiment, the pharmaceutical composition comprises a prodrug of a compound described herein, alone or in further combination with one or more other compounds described herein, or prodrugs thereof, and a pharmaceutically acceptable carrier.

In some embodiments, a pharmaceutical composition of the disclosure further comprises at least one additional pharmaceutically active agent other than a compound of the disclosure. The at least one additional pharmaceutically active agent can be, for example, an agent useful in the treatment of ischemia-reperfusion injury.

Pharmaceutical compositions can be prepared by combining one or more compounds with a pharmaceutically acceptable carrier and, optionally, one or more additional pharmaceutically active agents.

As stated above, an “effective amount” refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the disclosure being administered, the size of the subject, or the severity of the disease or condition. One of ordinary skill in the art can empirically determine the effective amount of a particular compound of the disclosure and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient’s peak or sustained plasma level of the drug. “Dose” and “dosage” are used interchangeably herein.

Generally, daily oral doses of a compound are, for human subjects, from about 0.01 milligrams/kg per day to 1000 milligrams/kg per day. Oral doses in the range of 0.5 to 50 milligrams/kg, in one or more administrations per day, can yield therapeutic results. Dosage may be adjusted appropriately to achieve desired drug levels, local or systemic, depending upon the mode of administration. For example, intravenous administration may vary from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods are well-known in the art and well within the capabilities of the ordinarily skilled artisan.

For clinical use, any compound of the disclosure can be administered in an amount equal or equivalent to 0.2-2000 milligram (mg) of compound per kilogram (kg) of body weight of the subject per day. The compounds of the disclosure can be administered in a dose equal or equivalent to 2-2000 mg of compound per kg body weight of the subject per day. The compounds of the disclosure can be administered in a dose equal or equivalent to 20-2000 mg of compound per kg body weight of the subject per day. The compounds of the disclosure can be administered in a dose equal or equivalent to 50-2000 mg of compound per kg body weight of the subject per day. The compounds of the disclosure can be administered in a dose equal or equivalent to 100-2000 mg of compound per kg body weight of the subject per day. The compounds of the disclosure can be administered in a dose equal or equivalent to 200-2000 mg of compound per kg body weight of the subject per day. Where a precursor or prodrug of the compounds of the disclosure is to be administered rather than the compound itself, it is administered in an amount that is equivalent to, i.e., sufficient to deliver, the above-stated amounts of the compounds of the invention.

The formulations of the compounds of the disclosure can be administered to human subjects in therapeutically effective amounts. Typical dose ranges are from about 0.01 microgram/kg to about 2 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments may be used to optimize the dose and dosing frequency for any particular compound.

The compounds of the disclosure can be administered at a concentration in the range from about 0.001 microgram/kg to greater than about 500 mg/kg. For example, the concentration may be 0.001 microgram/kg, 0.01 microgram/kg, 0.05 microgram/kg, 0.1 microgram/kg, 0.5 microgram/kg, 1.0 microgram/kg, 10.0 microgram/kg, 50.0 microgram/kg, 100.0 microgram/kg, 500 microgram/kg, 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed by the present invention.

The compounds of the disclosure can be administered at a dosage in the range from about 0.2 milligram/kg/day to greater than about 100 mg/kg/day. For example, the dosage may be 0.2 mg/kg/day to 100 mg/kg/day, 0.2 mg/kg/day to 50 mg/kg/day, 0.2 mg/kg/day to 25 mg/kg/day, 0.2 mg/kg/day to 10 mg/kg/day, 0.2 mg/kg/day to 7.5 mg/kg/day, 0.2 mg/kg/day to 5 mg/kg/day, 0.25 mg/kg/day to 100 mg/kg/day, 0.25 mg/kg/day to 50 mg/kg/day, 0.25 mg/kg/day to 2.5 mg/kg/day, 0.25 mg/kg/day to 10 mg/kg/day, 0.25 mg/kg/day to 7.5 mg/kg/day, 0.25 mg/kg/day to 5 mg/kg/day, 0.5 mg/kg/day to 50 mg/kg/day, 0.5 mg/kg/day to 25 mg/kg/day, 0.5 mg/kg/day to 20 mg/kg/day, 0.5 mg/kg/day to 15 mg/kg/day, 0.5 mg/kg/day to 10 mg/kg/day, 0.5 mg/kg/day to 7.5 mg/kg/day, 0.5 mg/kg/day to 5 mg/kg/day, 0.75 mg/kg/day to 50 mg/kg/day, 0.75 mg/kg/day to 25 mg/kg/day, 0.75 mg/kg/day to 20 mg/kg/day, 0.75 mg/kg/day to 15 mg/kg/day, 0.75 mg/kg/day to 10 mg/kg/day, 0.75 mg/kg/day to 7.5 mg/kg/day, 0.75 mg/kg/day to 5 mg/kg/day, 1.0 mg/kg/day to 50 mg/kg/day, 1.0 mg/kg/day to 25 mg/kg/day, 1.0 mg/kg/day to 20 mg/kg/day, 1.0 mg/kg/day to 15 mg/kg/day, 1.0 mg/kg/day to 10 mg/kg/day, 1.0 mg/kg/day to 7.5 mg/kg/day, 1.0 mg/kg/day to 5 mg/kg/day, 2 mg/kg/day to 50 mg/kg/day, 2 mg/kg/day to 25 mg/kg/day, 2 mg/kg/day to 20 mg/kg/day, 2 mg/kg/day to 15 mg/kg/day, 2 mg/kg/day to 10 mg/kg/day, 2 mg/kg/day to 7.5 mg/kg/day, or 2 mg/kg/day to 5 mg/kg/day.

The compounds of the disclosure can be administered at a dosage in the range from about 0.25 milligram/kg/day to about 25 mg/kg/day. For example, the dosage may be 0.25 mg/kg/day, 0.5 mg/kg/day, 0.75 mg/kg/day, 1.0 mg/kg/day, 1.25 mg/kg/day, 1.5 mg/kg/day, 1.75 mg/kg/day, 2.0 mg/kg/day, 2.25 mg/kg/day, 2.5 mg/kg/day, 2.75 mg/kg/day, 3.0 mg/kg/day, 3.25 mg/kg/day, 3.5 mg/kg/day, 3.75 mg/kg/day, 4.0 mg/kg/day, 4.25 mg/kg/day, 4.5 mg/kg/day, 4.75 mg/kg/day, 5 mg/kg/day, 5.5 mg/kg/day, 6.0 mg/kg/day, 6.5 mg/kg/day, 7.0 mg/kg/day, 7.5 mg/kg/day, 8.0 mg/kg/day, 8.5 mg/kg/day, 9.0 mg/kg/day, 9.5 mg/kg/day, 10 mg/kg/day, 11 mg/kg/day, 12 mg/kg/day. 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, 24 mg/kg/day, 25 mg/kg/day, 26 mg/kg/day, 27 mg/kg/day, 28 mg/kg/day, 29 mg/kg/day, 30 mg/kg/day, 31 mg/kg/day, 32 mg/kg/day, 33 mg/kg/day, 34 mg/kg/day, 35 mg/kg/day, 36 mg/kg/day, 37 mg/kg/day, 38 mg/kg/day, 39 mg/kg/day, 40 mg/kg/day, 41 mg/kg/day, 42 mg/kg/day, 43 mg/kg/day, 44 mg/kg/day, 45 mg/kg/day, 46 mg/kg/day, 47 mg/kg/day, 48 mg/kg/day, 49 mg/kg/day, or 50 mg/kg/day.

In various embodiments, the compound or precursor thereof is administered in concentrations that range from 0.01 micromolar to greater than or equal to 500 micromolar. For example, the dose may be 0.01 micromolar, 0.02 micromolar, 0.05 micromolar, 0.1 micromolar, 0.15 micromolar, 0.2 micromolar, 0.5 micromolar, 0.7 micromolar, 1.0 micromolar, 3.0 micromolar, 5.0 micromolar, 7.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 60.0 micromolar, 70.0 micromolar, 80.0 micromolar, 90.0 micromolar, 100.0 micromolar, 150.0 micromolar, 200.0 micromolar, 250.0 micromolar, 300.0 micromolar, 350.0 micromolar, 400.0 micromolar, 450.0 micromolar, to greater than about 500.0 micromolar or any incremental value thereof. It is to be understood that all values and ranges between these values and ranges are meant to be encompassed by the present invention.

In various embodiments, the compound or precursor thereof is administered at concentrations that range from 0.10 microgram/mL to 500.0 microgram/mL. For example, the concentration may be 0.10 microgram/mL, 0.50 microgram/mL, 1 microgram/mL, 2.0 microgram/mL, 5.0 microgram/mL, 10.0 microgram/mL, 20 microgram/mL, 25 microgram/mL, 30 microgram/mL, 35 microgram/mL, 40 microgram/mL, 45 microgram/mL, 50 microgram/mL, 60.0 microgram/mL, 70.0 microgram/mL, 80.0 microgram/mL, 90.0 microgram/mL, 100.0 microgram/mL, 150.0 microgram/mL, 200.0 microgram/mL, 250.0 g/mL, 250.0 micro gram/mL, 300.0 microgram/mL, 350.0 microgram/mL, 400.0 microgram/mL, 450.0 microgram/mL, to greater than about 500.0 microgram/mL or any incremental value thereof. It is to be understood that all values and ranges between these values and ranges are meant to be encompassed by the present invention.

The formulations of the disclosure can be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition may be accomplished by any means known to the skilled artisan. Routes of administration include, but are not limited to, intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound of the disclosure can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well-known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also contemplated are oral dosage forms of the compounds of the disclosure. The compounds of the disclosure may be chemically modified so that oral delivery of the derivative is efficacious. Generally, the chemical modification contemplated is the attachment of at least one moiety to the compound itself, where said moiety permits (a) inhibition of acid hydrolysis; and (b) uptake into the blood stream from the stomach or intestine. Also desired is the increase in overall stability of the compounds and increase in circulation time in the body. Examples of such moieties include polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. For pharmaceutical usage, as indicated above, polyethylene glycol moieties are suitable.

The location of release of a compound of the disclosure may be the stomach, the small intestine (the duodenum, the jejunum, or the ileum), or the large intestine. One skilled in the art has available formulations which will not dissolve in the stomach yet will release the material in the duodenum or elsewhere in the intestine. The release can avoid the deleterious effects of the stomach environment, either by protection of the compound of the disclosure or by release of the compound beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the disclosure may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include, but are not limited to, stearic acid including its magnesium and calcium salts, polytetrafluoroethylene (PTFE), liquid paraffin, vegetable oils and waxes. Soluble lubricants may also be used, such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the disclosure or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well-defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, a compound may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers, such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, R., *Science* 249:1527-33 (1990).

The compound of the disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the disclosure contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

The therapeutic agent(s), including specifically but not limited to a compound of the disclosure, may be provided in particles. Particles as used herein means nanoparticles or microparticles (or in some instances larger particles) which can consist in whole or in part of the compound of the disclosure or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodibie, biodegradable, or nonbiodegradable material or combinations thereof. The particles may be microcapsules which contain the compound of the disclosure in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney et al., *Macromolecules* 26:581-587 (1993), the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used in its conventional sense to refer to a drug formulation that provides for gradual release of a drug over an extended period of time, and that can result in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and up to 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the disclosure contained herein in view of information known to the ordinarily skilled artisan, and may be made without departing from the scope of the disclosure or any embodiment thereof.

EXAMPLES

The disclosure now being generally described, it will be more readily understood by reference to the following examples, which are included merely for purposes of illustration of various aspects and embodiments of the present disclosure and are not intended to limit the disclosure.

Synthesis of PLE Derivatives

Figure 3:
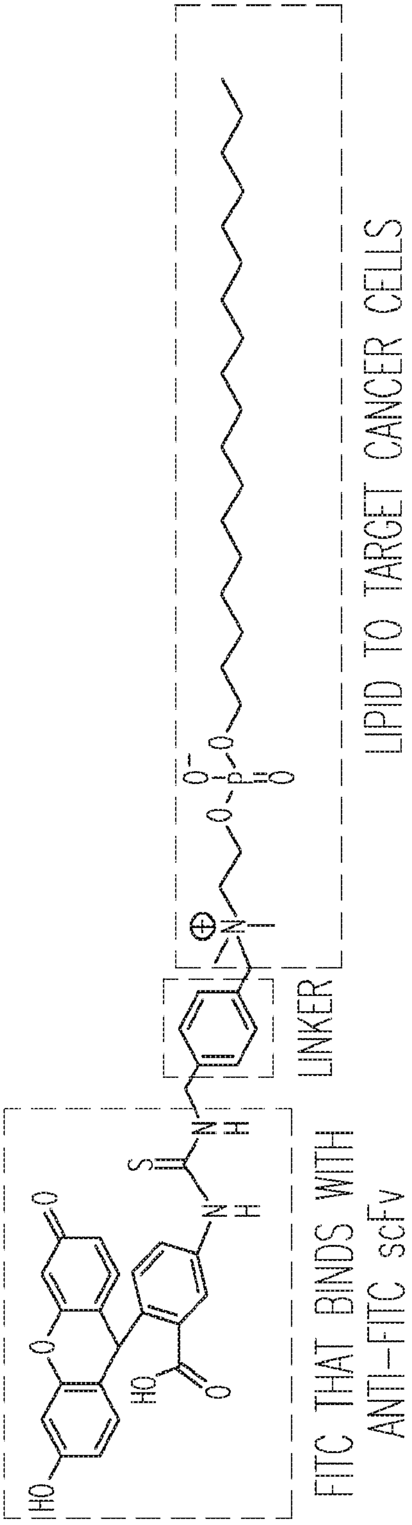
FIG. 3 is the structure of Purdue fluorescein-lipid conjugate (Purdue FL-PLE).
Figure 4:
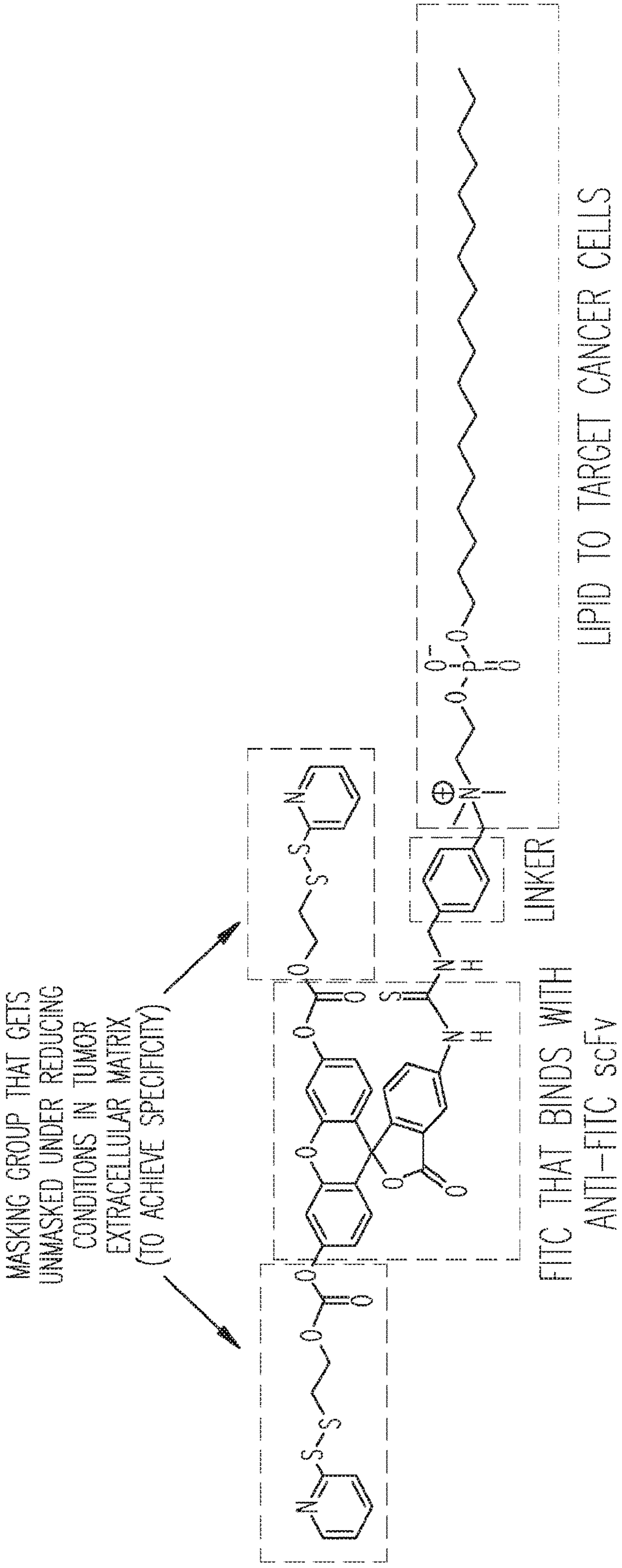
FIG. 4 is the structure of Purdue Pro-fluorescein-lipid conjugate (Purdue Pro-FL-PLE).
Figure 5:
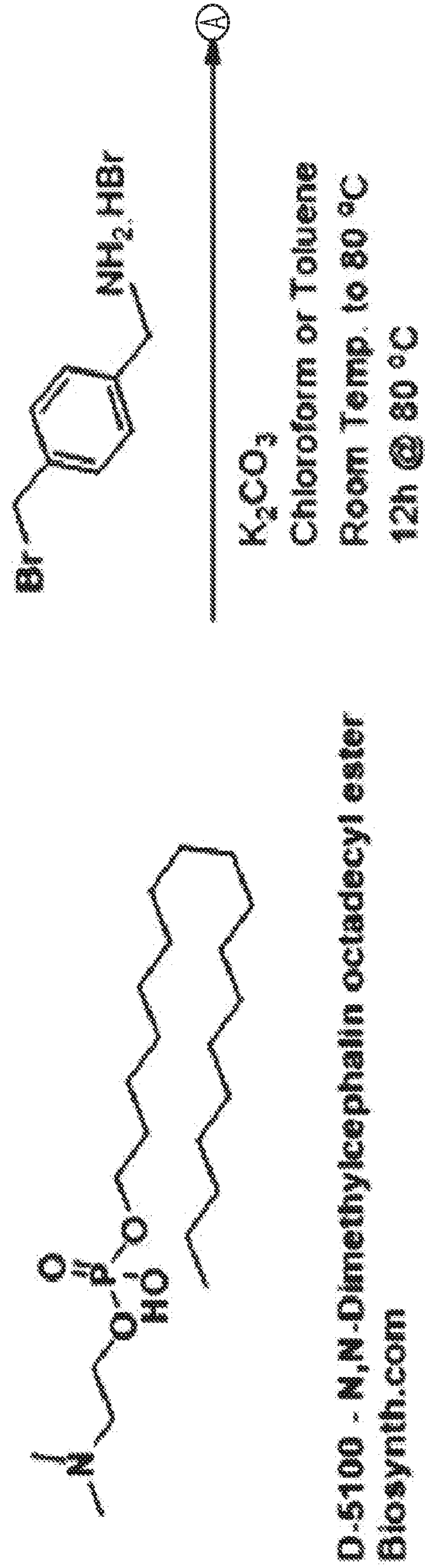
FIG. 5 is a synthetic scheme of Purdue fluorescein-lipid conjugate (Purdue FL-PLE Pro-FL-PLE).
Figure 5:
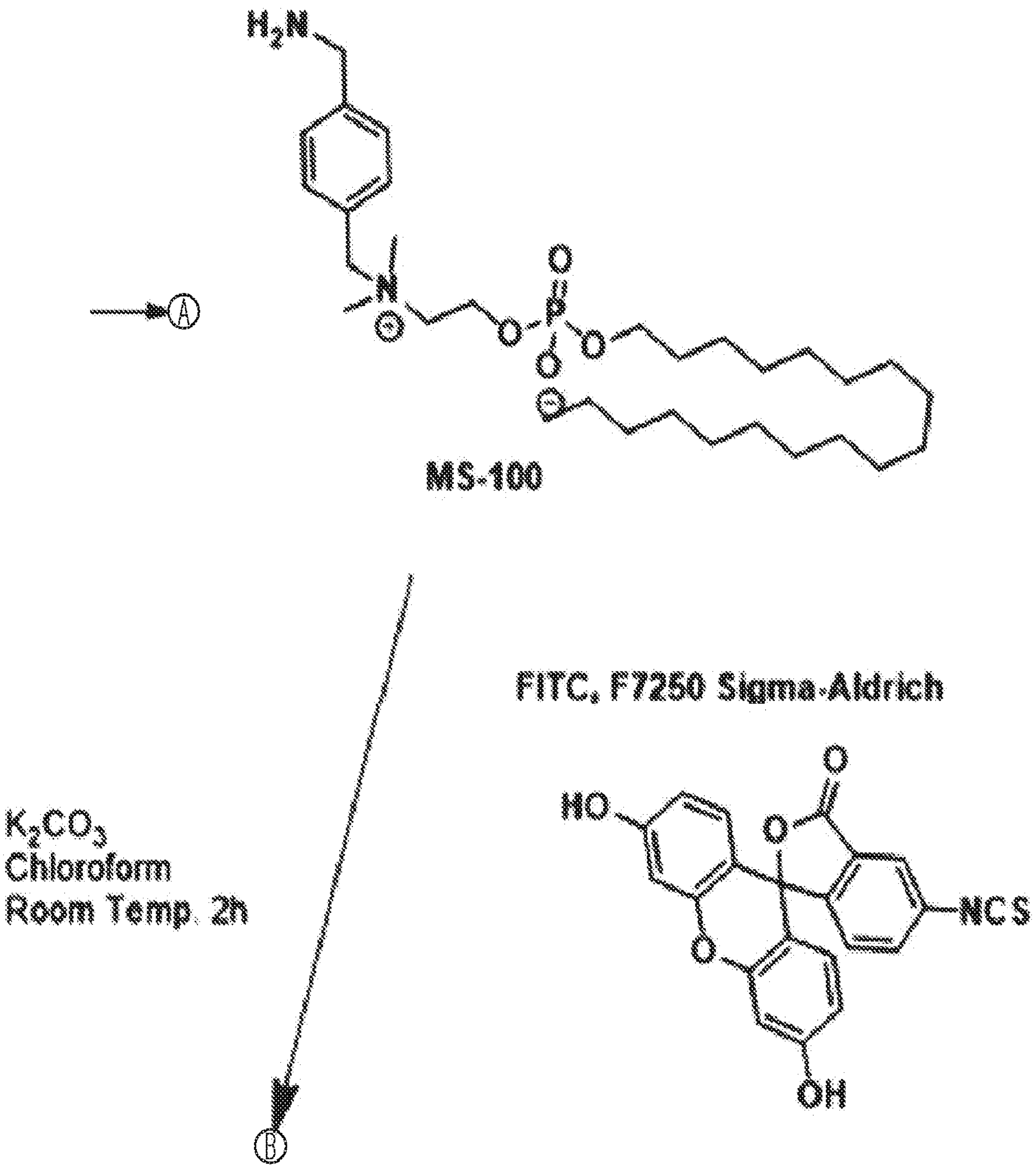
Figure 5:
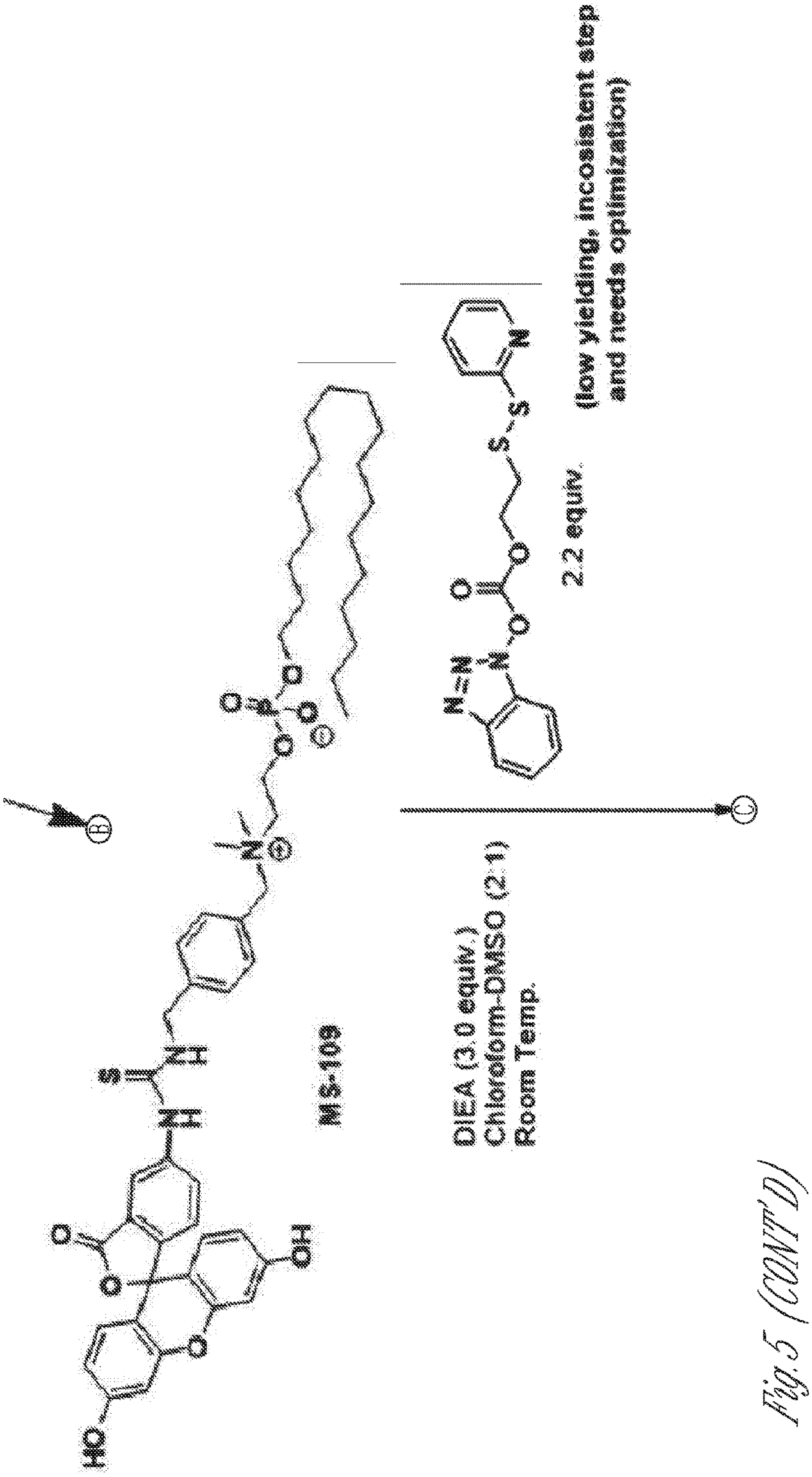
Figure 5:
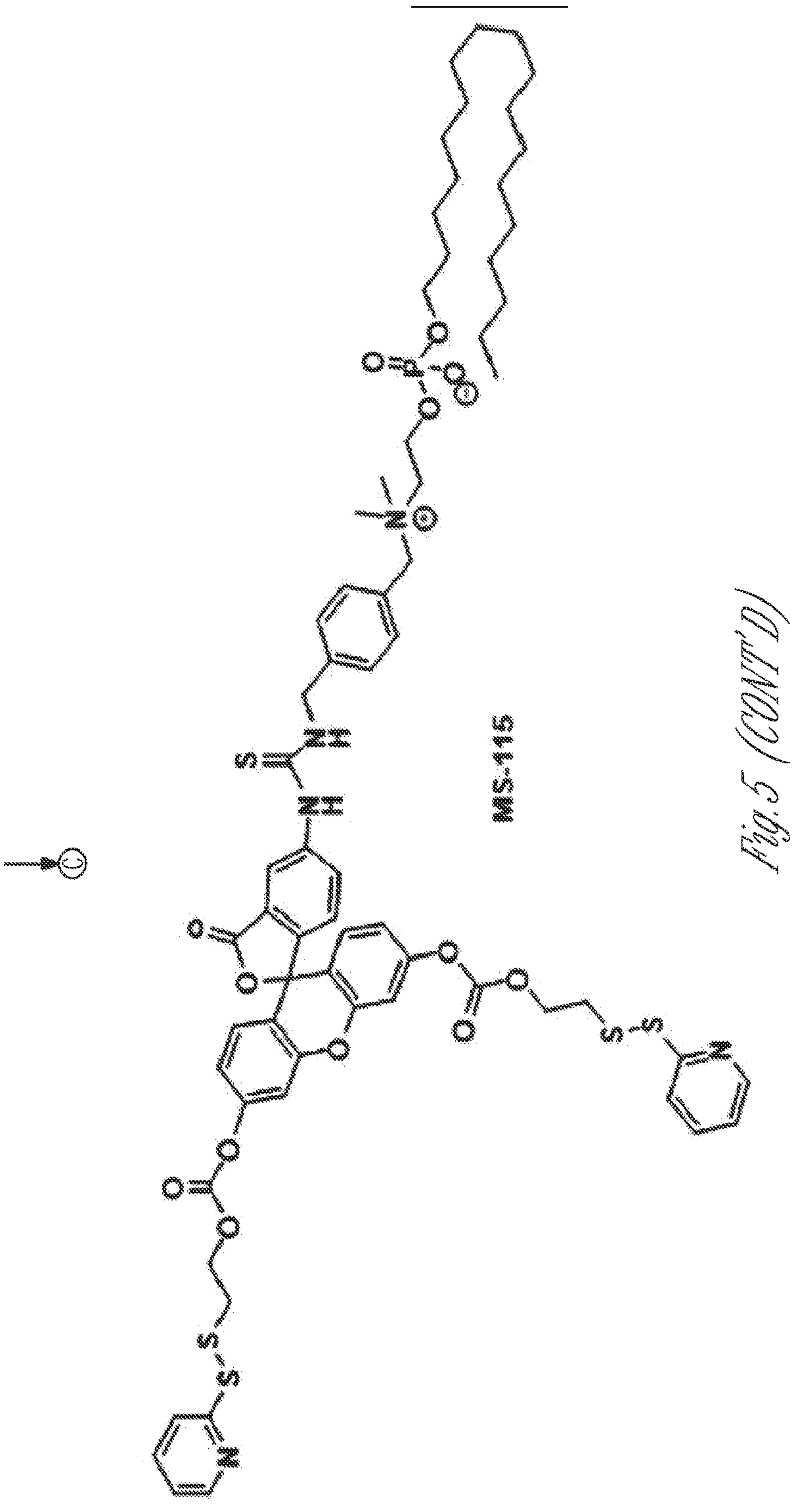

The synthesis of xylene-based FL-PLE (FIG. 3) and Pro-FL-PLE (FIG. 4) were accomplished in 2-3 steps (FIG. 5).

Figure 6:
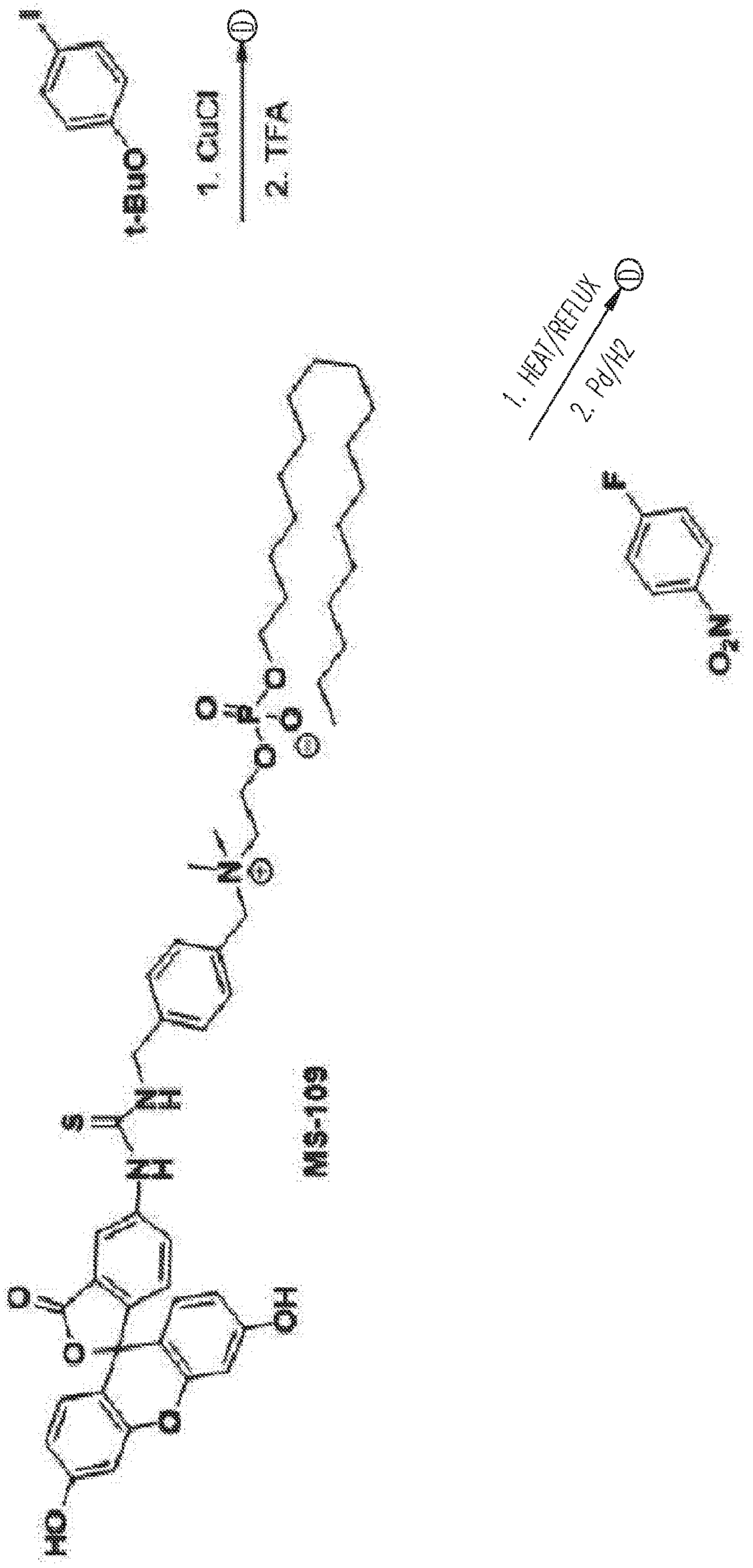
FIG. 6 is a synthetic scheme of FITC-PLE protected with a reactive oxygen species (ROS)-cleavable group.
Figure 6:
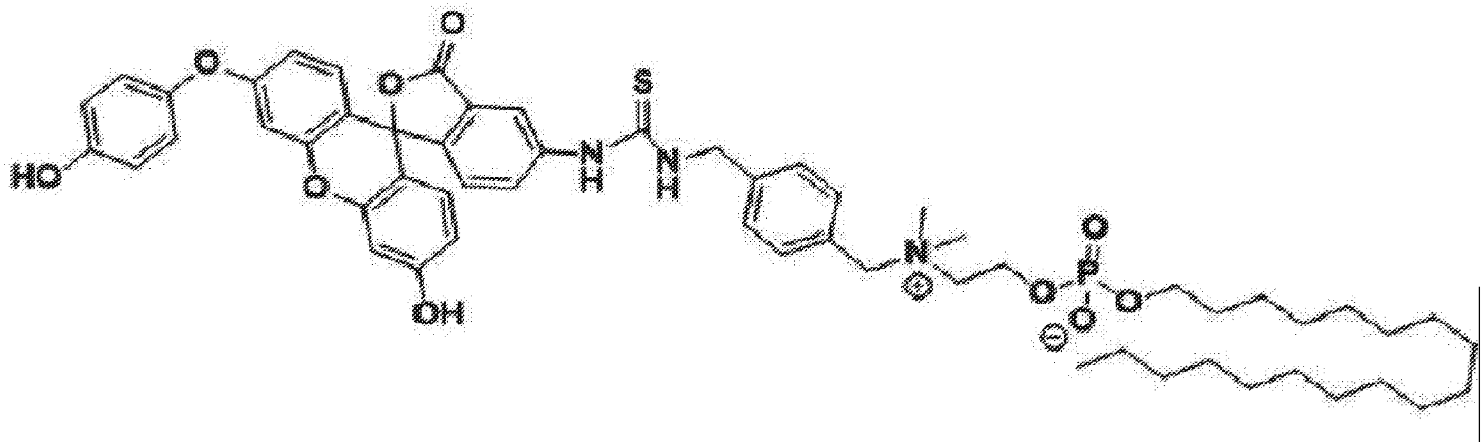
Figure 6:
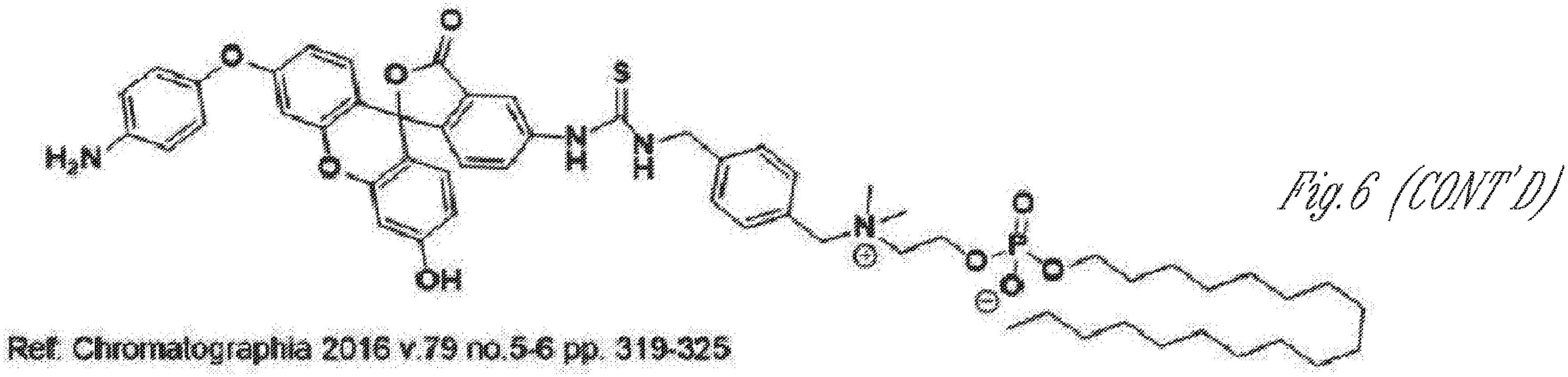
Figure 7:
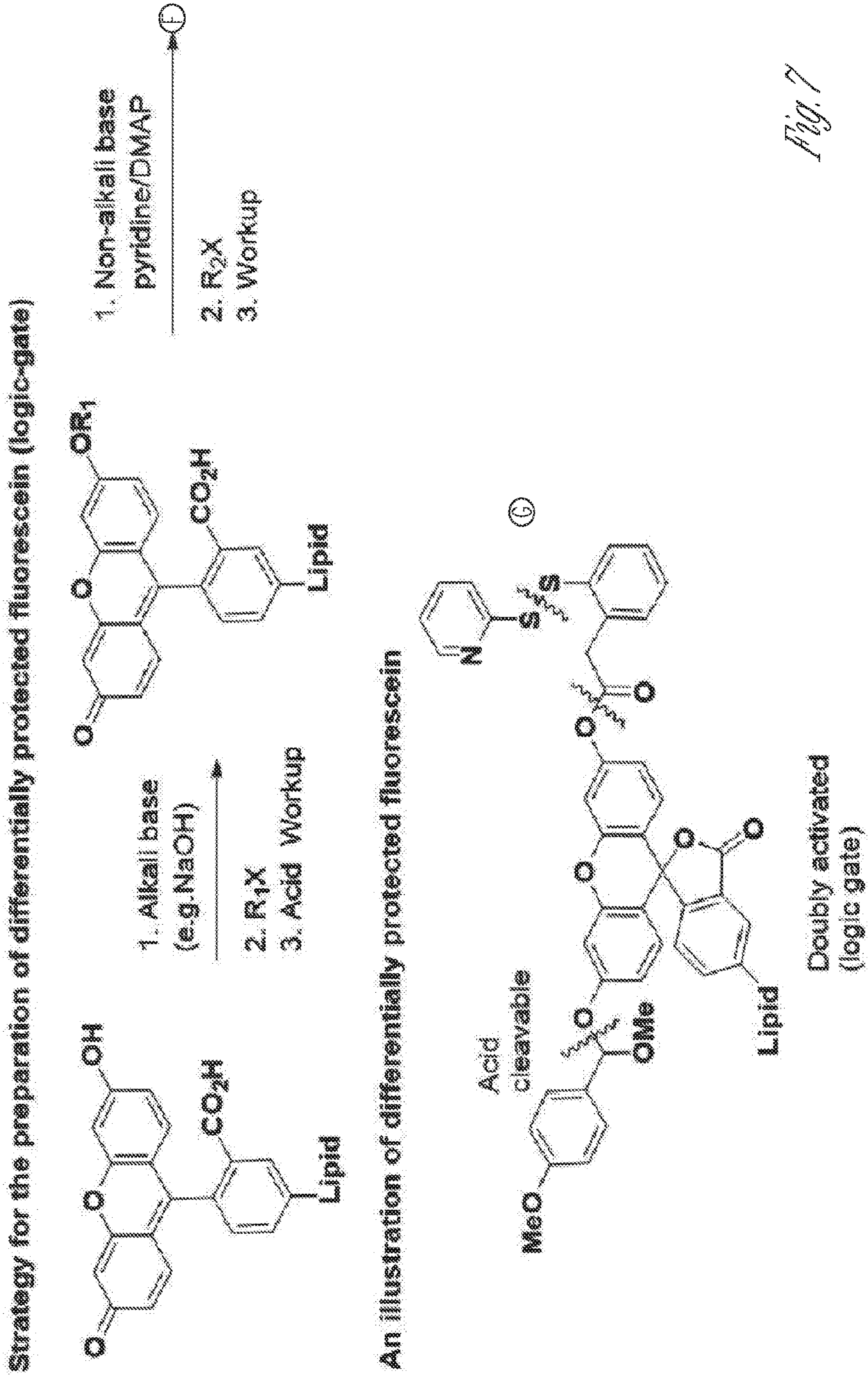
FIG. 7 is a synthetic scheme of FITC-PLE with dual protecting groups (dual gate approach or logic gate approach).
Figure 7:
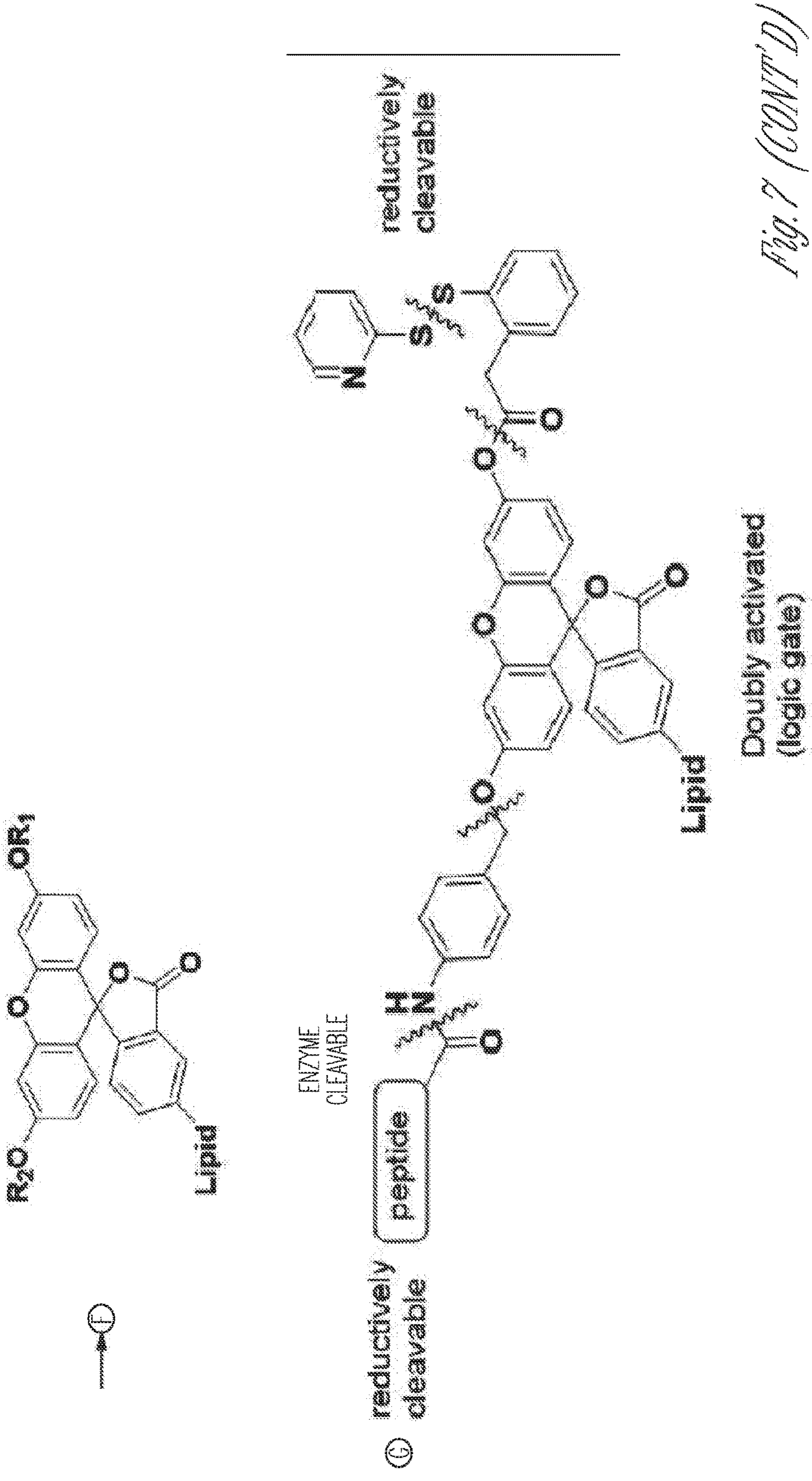

Protected version of the lipid-fluorescein conjugates that are cleavable by ROS (FIG. 6), enzymes, and low pH or any other triggers in the tumor microenvironment can also be synthesized in a similar fashion (FIG. 6). The synthesis is also amenable for making Pro-FL-PLEs containing two different protecting groups for dual specificity (a logic gate or dual gate approach, FIG. 7).

Synthesis and Characterization

Synthetic Procedure for Lipid-Linker (MS-100), Lipid-FITC (MS-109) and Masked Lipid-FITC (MS-115)

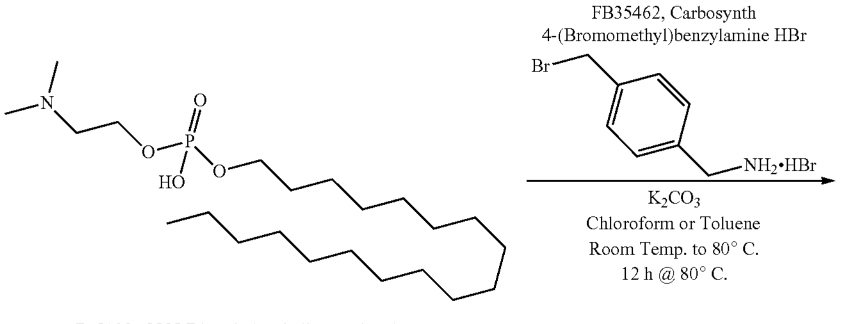

D-5100 - N,N-Dimethylcephalin octadecyl ester
Biosynth.com

-continued

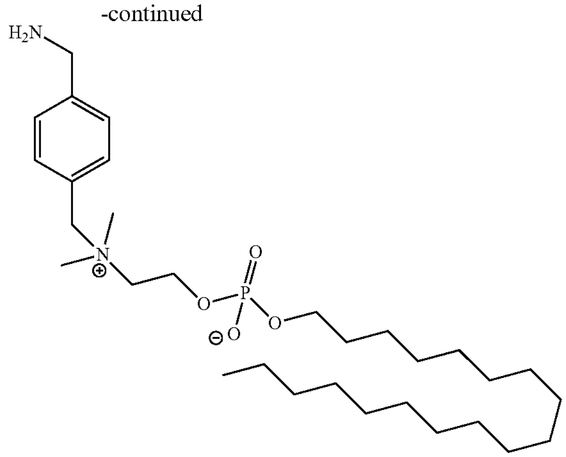

MS-100

Preparation of lipid MS-100. N,N-Dimethylcephalin octadecyl ester (5 mg, 0.011 mmol, 1 equiv.) and 4-(bromomethyl)benzylamine·HBr salt (3.4 mg, 0.012 mmol, 1.1 equiv.) were dissolved in 0.3 mL of chloroform (or toluene). After adding potassium carbonate (1.5 mg, 0.011 mmol, 1 equiv.) the resulting mixture was heated to 80° C. and stirred for 12 h. The completion of the reaction was monitored by LC-MS (mobile phase of A=20 mM ammonium bicarbonate buffer, pH 7; B=acetonitrile; gradient 0-100% B in 7 min, 0.75 mL $min^{-1}$, λ=220 nm). The crude product was taken to the next step.

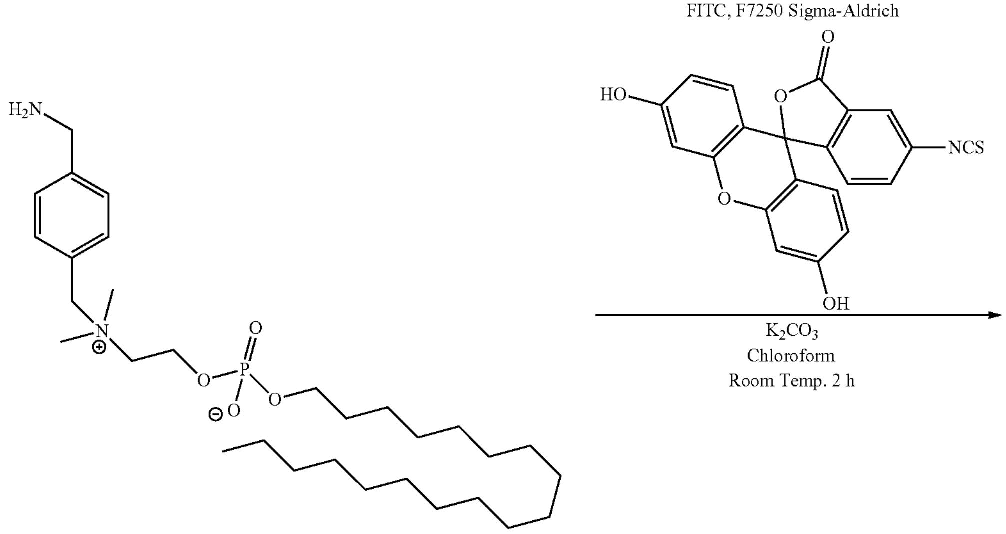

Crude MS-100 1.0 equiv.

-continued

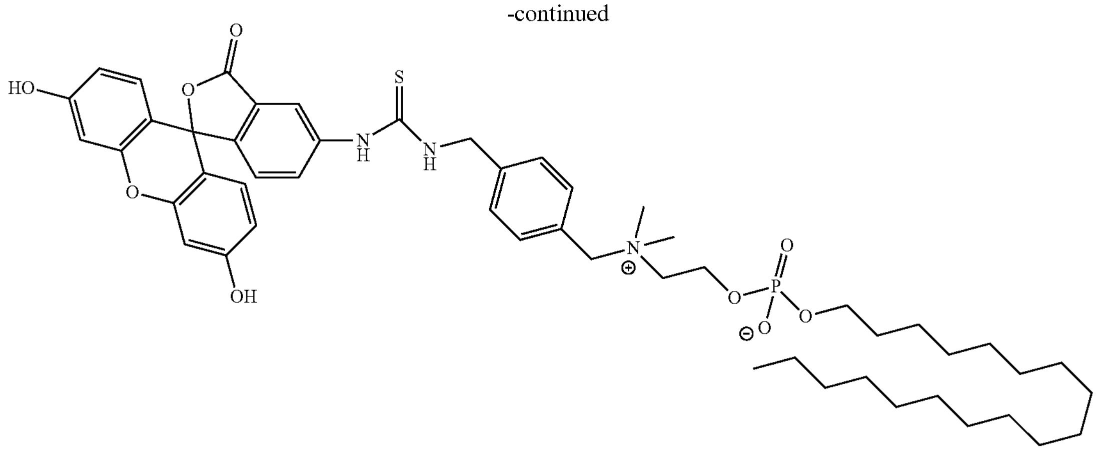

MS-109

Preparation of lipid-HTC MS-109. The crude lipid MS-100 (0.011 mmol) from the above reaction was reacted with fluorescein isothiocyanate (4.3 mg, 0.011 mmol, 1.0 equiv.) and potassium carbonate (4.5 mg, 0.033 mmol, 3.0 equiv.) in 0.3 mL of chloroform. The mixture was stirred at room temperature for 2 h. The completion of the reaction was monitored by LC-MS (retention time=4.2 min, mobile phase of A=20 mM ammonium bicarbonate buffer, pH 7; B=acetonitrile; gradient 0-100% B in 7 min, 0.75 mL min−1, λ=280 nm). The solvent was evaporated by passing dry nitrogen gas. The resulting mixture was dissolved in DMSO (note: sufficient amount of DMSO was added to make a less viscous solution. The solution was filtered through 0.45 micron filter before loading on the HPLC. Any vigorous shaking or pipetting should be avoided to prevent formation of emulsions). The solution was then purified by HPLC (mobile phase of A=20 mM ammonium acetate buffer, pH 7; B=acetonitrile; gradient 0-100% B in 35 min, 12 mL min−1, λ=280 nm). The fractions with pure product were combined and lyophilized to provide 6 mg (59% yield) of MS409.

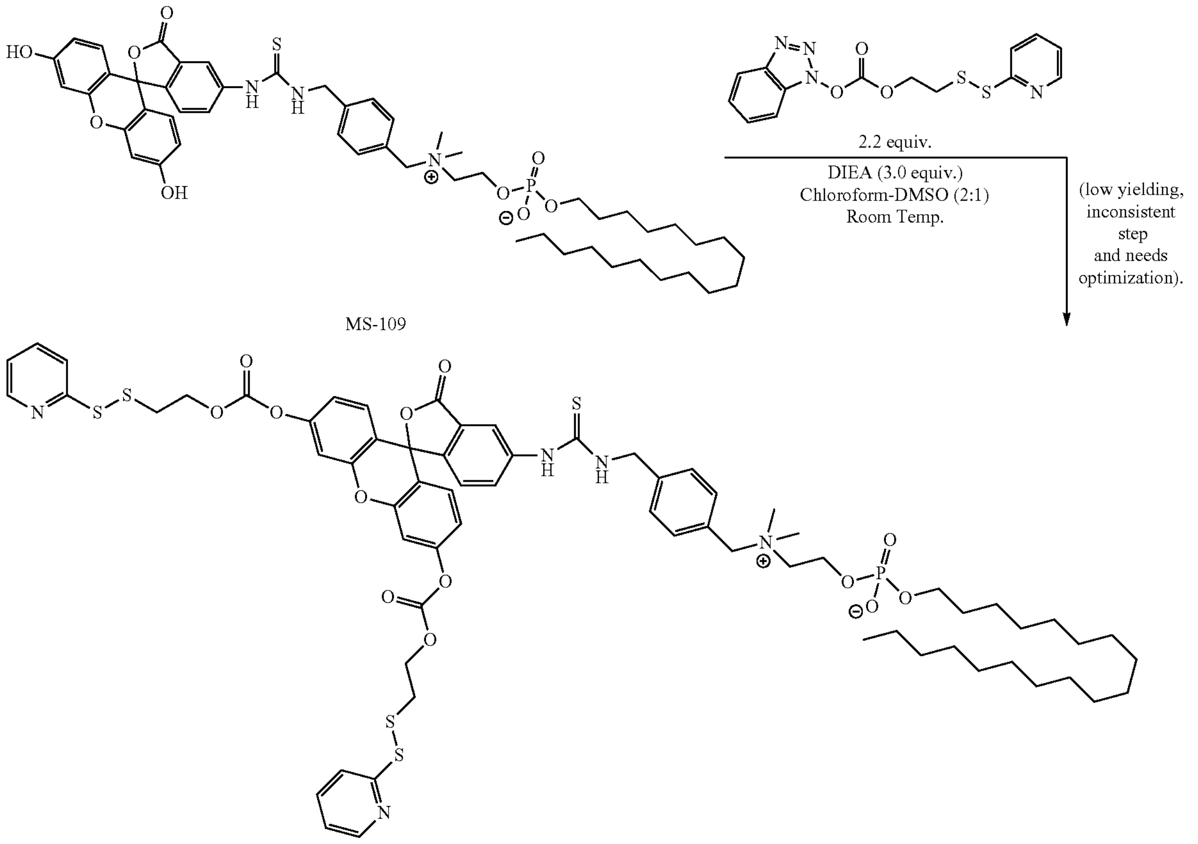

MS-109

MS-115

Preparation of masked lipid-FITC MS-115. The lipid-FITC MS-109 (4 mg, 0.004 mmol) was reacted with 1H-benzo[d][1,2,3]triazol-1-yl (2-(pyridin-2-yldisulfaneyl) ethyl) carbonate (3.5 mg, 0.010 mmol, 2.2 equiv.) and DMA (3.0 equiv.) in 0.15 mL of chloroform-DMSO (2:1). The mixture was stirred at room temperature for 1:2 h. The completion of the reaction was monitored by LC-MS (retention time=5.8 min, mobile phase of A=20 mM ammonium bicarbonate buffer, pH 7; B=acetonitrile; gradient 0-100% B in 7 min, 0.75 mL min−1, λ=280 nm). The solvent was evaporated by passing dry nitrogen gas. The resulting mixture was dissolved in DMSO (note: sufficient amount of DMSO was added to make a less viscous solution. The solution was filtered through (145 micron filter before loading on the HPLC. Any vigorous shaking or pipetting should be avoided to prevent formation of emulsions). The solution was then purified by HPLC. (retention time=mobile phase of A=20 mM ammonium acetate buffer, pH 7; B=acetonitrile; gradient 0-100% B in 35 min, 12 mL min−1, λ=280 nm). The fractions with pure product were combined and lyophilized to provide 1 mg (18%) of MS-115.

1H-benzo[d][1,2,3]triazol-1-yl (2-(pyridin-2-yldisulfaneyl)ethyl) carbonate was prepared according to the protocol reported in Journal of Medicinal Chemistry, 53(21), 7767-7777; 2010.

Numbered Embodiments

Embodiment 1 relates to a compound of Formula (I) or (II):

(I)

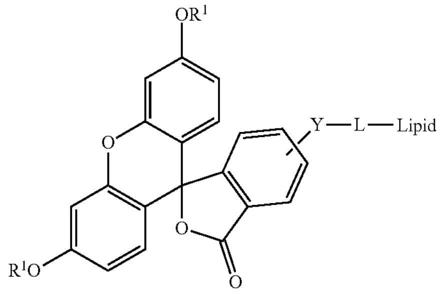

(II)

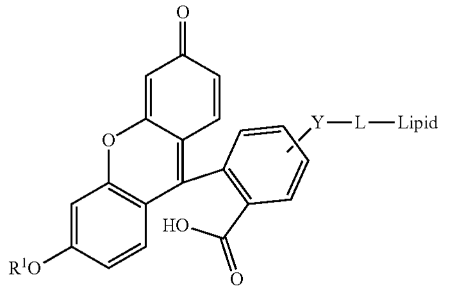

wherein:

$R^1$ is independently H, or a protecting group that is deprotected in tumor extracellular matrix;

Y is absent, —N(H)C(S)N(H)—, —N(H)C(O)N(H)—, —N(H)C(O)—, —N(H)C(S)—, —C(O)—NH—, —C(S)N(H)—, —C(O)O—, —N(H)—, —S(O)N(H)—, —$S(O)_2$N(H)—, —$S(O)_3$—, —$P(O)_2$N(H)—, —$P(O)_3$—;

L is a linker; and

Lipid is a cancer-cell targeting lipid; and at least one $R^1$ is a protecting group;

or a pharmaceutically acceptable salt thereof.

Embodiment 2 relates to a compound of Embodiment 1, wherein both $R^1$ are a protecting group.

Embodiment 3 relates to a compound of Embodiment 1, wherein each $R^1$ are different.

Embodiment 4 relates to a compound of Embodiment 1, wherein both $R^1$ are the same.

Embodiment 5 relates to a compound of any one of Embodiments 1-4, wherein the protecting group is a ROS-cleavable group.

Embodiment 6 relates to a compound of any one of Embodiments 1-4, wherein the protecting group is an acid-cleavable group.

Embodiment 7 relates to a compound of any one of Embodiments 1-4, wherein the protecting group is reductively cleaved.

Embodiment 8 relates to a compound of any one of Embodiments 1-4, wherein the protecting group is an enzyme-cleavable group.

Embodiment 9 relates to a compound of any one of Embodiments 1-4, wherein the protecting group is cleavable at low pH.

Embodiment 10 relates to a compound of any one of Embodiments 1-4, wherein the protecting group is cleaved by any triggers in the tumor microenvironment.

Embodiment 11 relates to a compound of any one of Embodiments 1-4, wherein the protecting group is

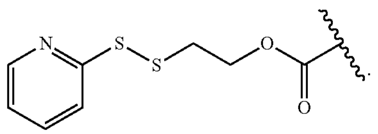 [SMILES: *C(=O)OCCSSc1ccccn1]

Embodiment 12 relates to a compound of any one of Embodiments 1-4, wherein the protecting group is

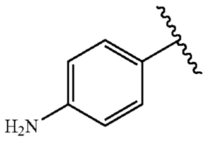

or

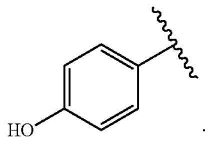

Embodiment 13 relates to a compound of any one of Embodiments 1-12, wherein a UV-active linker.

Embodiment 14 relates to a compound of any one of Embodiments 1-12, wherein L is a chromophore.

Embodiment 15 relates to a compound of any one of Embodiments 1-12, wherein L is

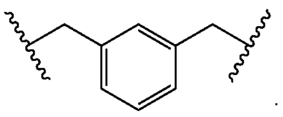

Embodiment 16 relates to a compound of any one of Embodiments 1-15, wherein Lipid can be a lipid comprising 5-30 carbon atoms.

Embodiment 17 relates to a compound of any one of Embodiments 1-16, wherein Lipid is
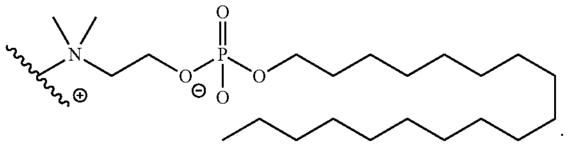
Embodiment 18 relates to a compound of Embodiment 1, wherein the compound is
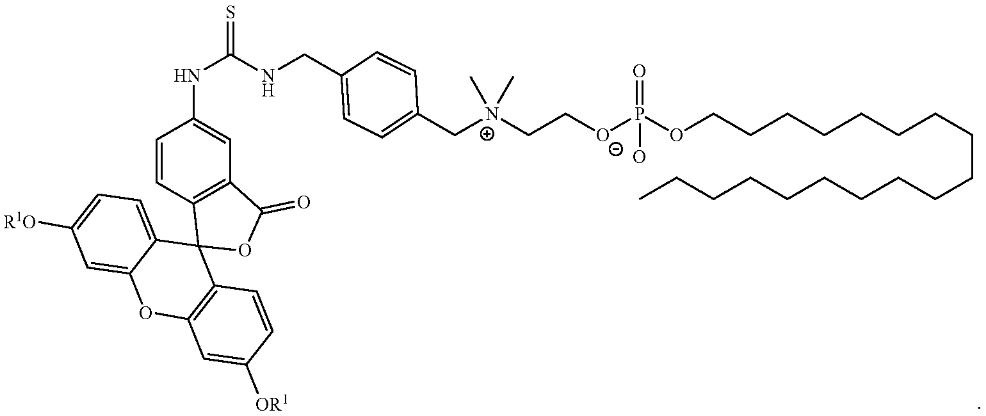
Embodiment 19 relates to a compound of Embodiment 1, wherein the compound is
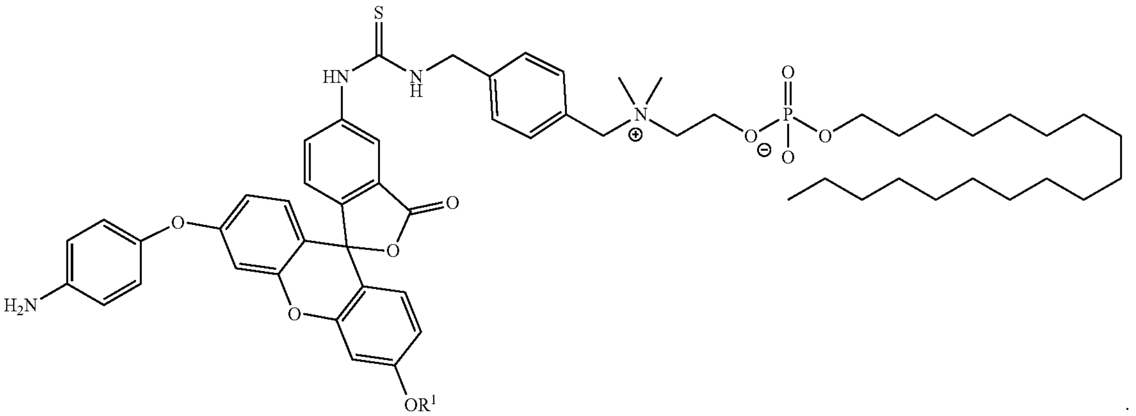

Embodiment 20 relates to a compound of Embodiment 1, wherein the compound is

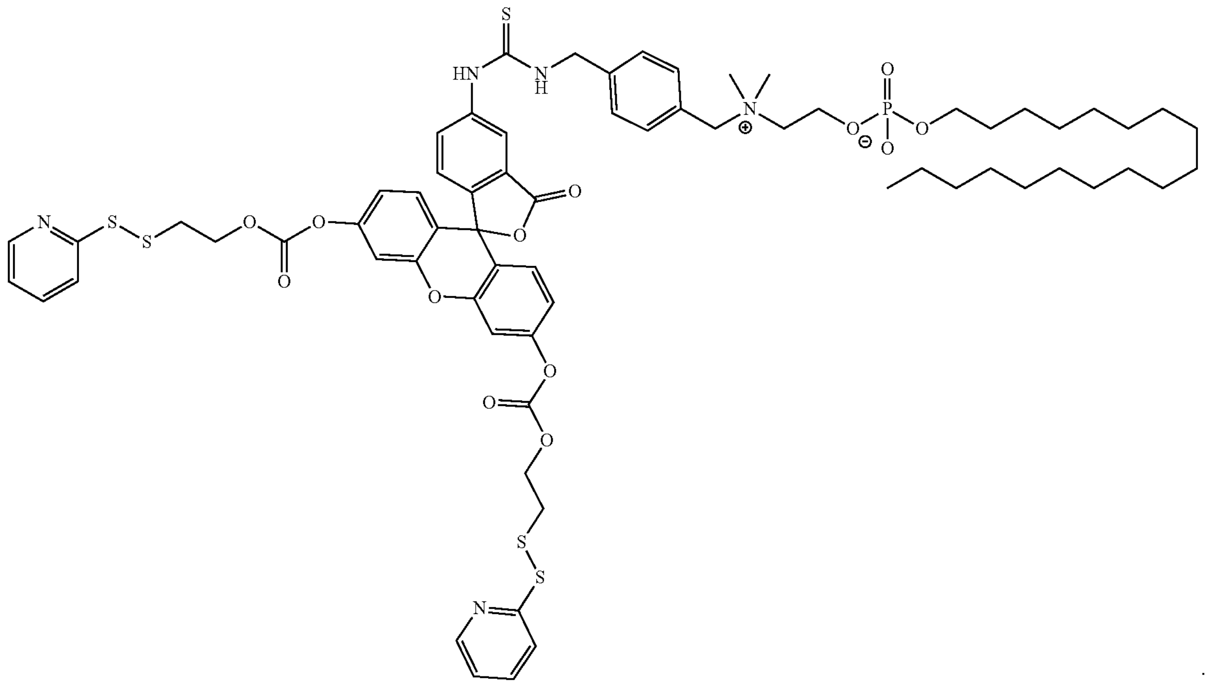

.

Embodiment relates to a pharmaceutical composition comprising a compound of any one of Embodiments 1-20, and a pharmaceutical acceptable carrier.

Embodiment 22 relates to a method of treating cancer in a subject suffering therefrom, comprising administering to the subject a therapeutically effective amount of a compound of any one of Embodiments 1-20, or a pharmaceutical composition of Embodiment 18, whereupon the subject is treated for cancer.

Embodiment 23 relates to the method of Embodiment 22, wherein the cancer is glioma.

Embodiment 24 relates to a method of making a lipid-FITC comprising:

reacting a lipid with fluorescein isothiocyanate and a base in a solvent.

Embodiment 25 relates a method of making a masked lipid-FITC comprising:

reacting a lipid-FITC with a protecting group and a base in a solvent.

Embodiment 26 relates to a method of making a FITC-PLE with heterogeneous protecting groups comprising: A method of making a FITC-PLE with heterogeneous protecting groups comprising:

i) conjugating a lipid to aminobenzyl bromide to produce the quaternary ammonium intermediate, ii) coupling of the intermediate to fluorescein isothiocyanate to produce a xylene-based FL- and iii) optionally protecting a Pro-FL-PLE.

Embodiment 27 relates the method of any one of Embodiments 24-26, wherein the base is potassium carbonate, sodium carbonate, trialkylamine, pyridine, dimethylaminopyridine, potassium hydroxide, sodium hydroxide or a combination thereof.

Embodiment 28 relates the method of any one of Embodiments 24-26, wherein the base is potassium carbonate.

Embodiment 29 relates the method of any of one of Embodiments 24-28, wherein the solvent is chloroform, tetrahydrofuran, carbon tetrachloride, dichloromethane, dimethyl sulfoxide, dimethyl formamide, acetonitrile, pyridine, water, or any combination of thereof.

Embodiment 30 relates the method of any of one of Embodiments 24-28, wherein the solvent is chloroform.

Embodiment 31 relates the method of Embodiment 30, wherein the base is DIEA.

Embodiment 32 relates the method of any one of Embodiments 24-26, wherein the solvent is chloroform-DMSO (2:1).

INCORPORATION BY REFERENCE

All the patents, patent application publications, journal articles, books and other publications cited herein are hereby incorporated by reference.

EQUIVALENTS

Those skilled in the art will recognize or be able to ascertain using no more than routine experimentation, many equivalents to the various embodiments of the disclosure described herein. Such equivalents are encompassed by the following claims.

We claim:

1. A compound of Formula (I) or (II):

(I)

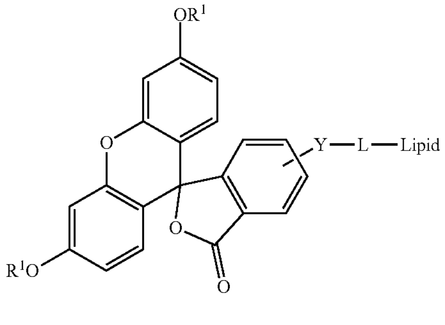

-continued (II)

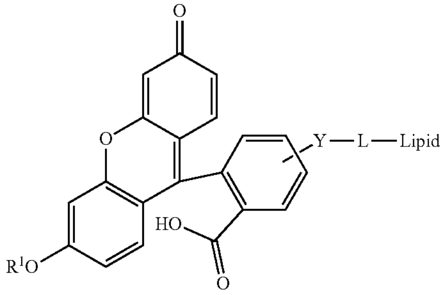

or a pharmaceutically acceptable salt thereof;

wherein:

$R^1$ is independently H, or a protecting group that is deprotected in tumor extracellular matrix, wherein at least one $R^1$ group is a protecting group;

Y is absent, —N(H)C(S)N(H)—, —N(H)C(O)N(H)—, —N(H)C(O)—, —N(H)C(S)—, —C(O)—N(H)—, —C(S)N(H)—, —C(O)O—, —N(H)—, —S(O)N(H)—, —$S(O)_2N(H)$—, —$S(O)_3$—, —$P(O)_2N(H)$—, or —$P(O)_3$—;

L is a linker; and

Lipid is a cancer-cell targeting lipid; and at least one $R^1$ is a protecting group;

wherein the protecting group is:

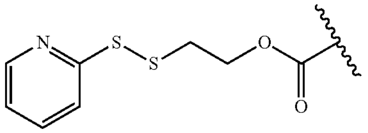 [SMILES: *C(=O)OCCSSc1ccccn1]

or a pharmaceutically acceptable salt thereof.

2. The compound of claim 1, wherein both $R^1$ groups in the compound of Formula (I) are protecting groups.

3. The compound of claim 1, wherein Lis an ultraviolet (UV)-active linker.

4. The compound of claim 1, wherein L is a chromophore.

5. A compound of Formula (I) or (II):

(I)

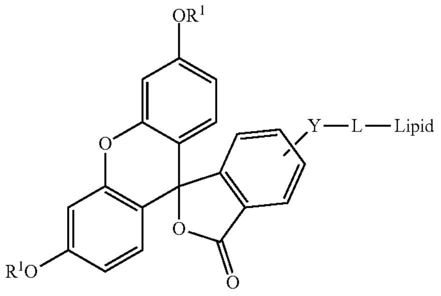

-continued (II)

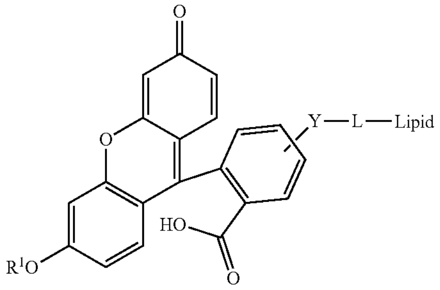

or a pharmaceutically acceptable salt thereof, wherein:

$R^1$ is independently H, or a protecting group that is deprotected in tumor extracellular matrix, wherein at least one $R^1$ group is a protecting group;

Y is absent, —N(H)C(S)N(H)—, —N(H)C(O)N(H)—, —N(H)C(O)—, —N(H)C(S)—, —C(O)—N(H)—, —C(S)N(H)—, —C(O)O—, —N(H)—, —S(O)N(H)—, —$S(O)_2N(H)$—, —S(O)—, —$P(O)_2N(H)$—, or —$P(O)_3$—;

L is:

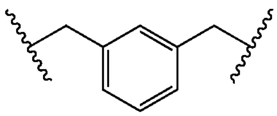

;

and

Lipid is a cancer-cell targeting lipid.

6. The compound of claim 1, wherein Lipid is:

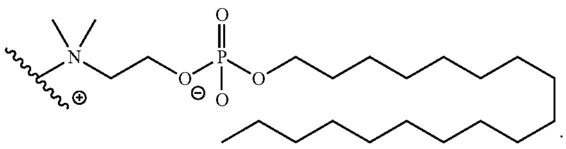

.

7. The compound of claim 5, wherein Lipid is:

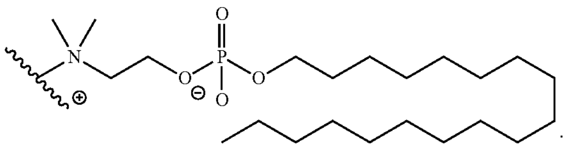

.

8. The compound of claim 1, wherein the compound is:
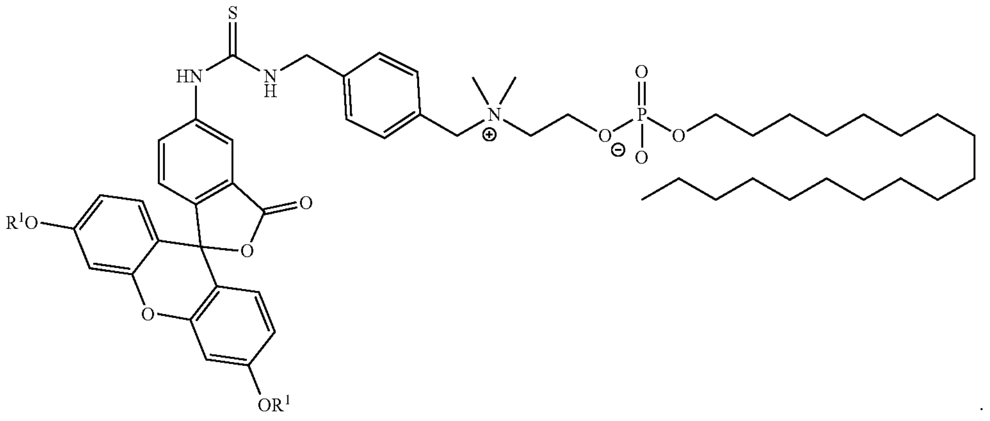
9. The compound of claim 5, wherein the compound is:
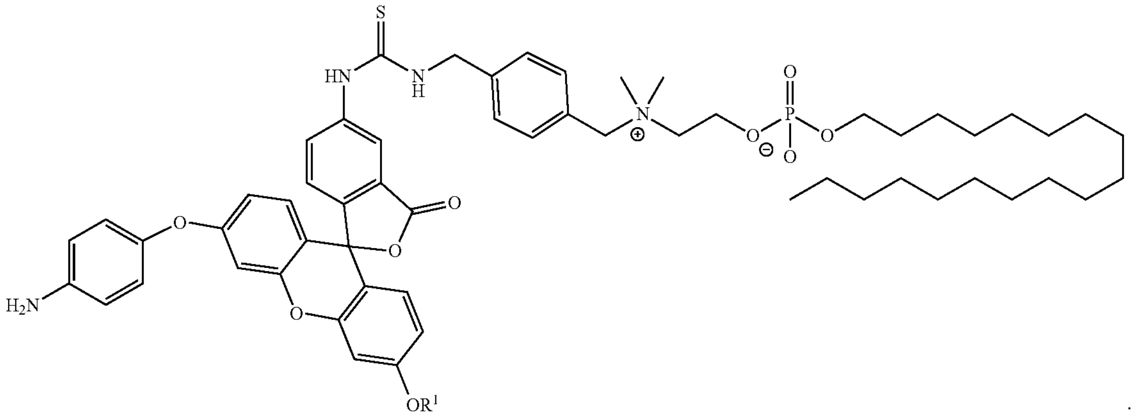
10. The compound of claim 1, wherein the compound is:
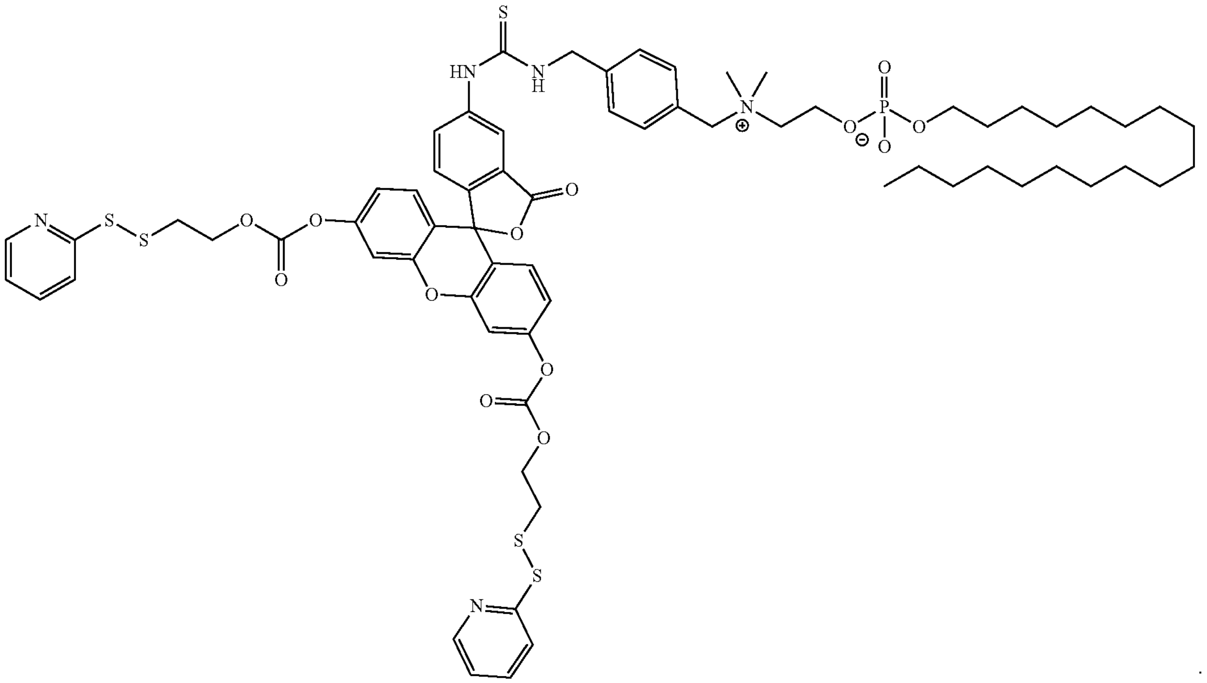

11. A pharmaceutical composition comprising a compound of claim 1, and a pharmaceutical acceptable carrier.
12. The compound of claim 5, wherein the protecting group is a reactive oxygen species (ROS)-cleavable group.
13. The compound of claim 5, wherein the protecting group is:
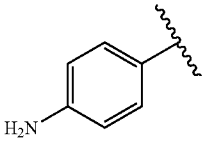
or
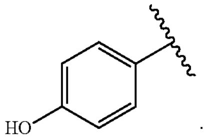
.
14. The compound of claim 5, wherein the compound is:
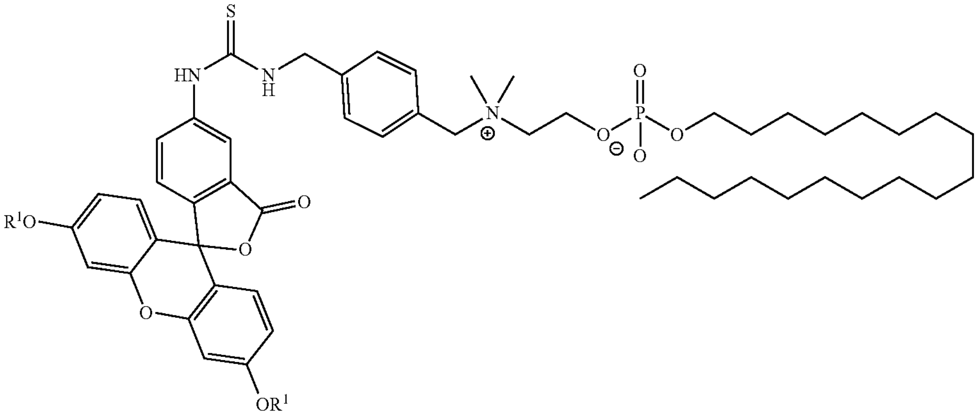
.
15. The compound of claim 5, wherein the compound is:
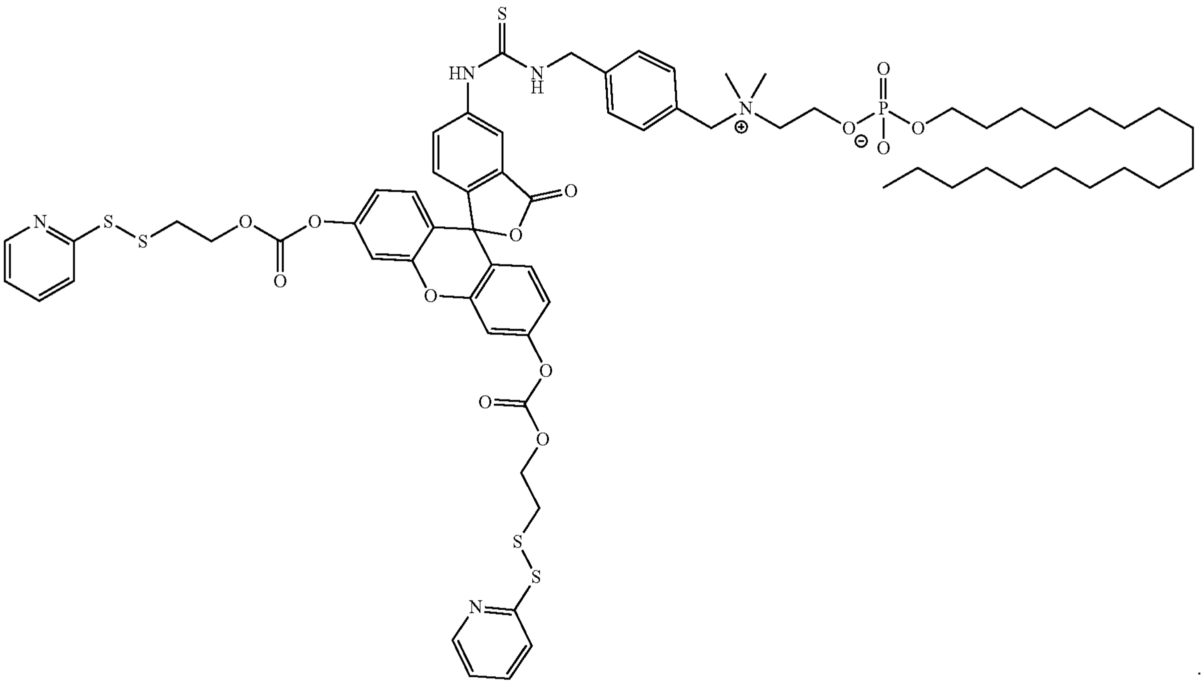
.

16. A pharmaceutical composition comprising a compound of claim 5, and a pharmaceutical acceptable carrier.

* * * * *